(12) United States Patent
Buelow et al.

(10) Patent No.: US 7,919,672 B2
(45) Date of Patent: Apr. 5, 2011

(54) SUPPRESSION OF B-CELL APOPTOSIS IN TRANSGENIC ANIMALS EXPRESSING HUMANIZED IMMUNOGLOBULIN

(75) Inventors: Roland Buelow, Palo Alto, CA (US); Josef Platzer, Geretsfied (DE)

(73) Assignee: Therapeutic Human Polyclonals, Inc., Mountain View, CA (US)

( * ) Notice: Subject to any disclaimer, the term of this patent is extended or adjusted under 35 U.S.C. 154(b) by 741 days.

(21) Appl. No.: 11/498,571

(22) Filed: Aug. 2, 2006

(65) Prior Publication Data

US 2007/0033661 A1    Feb. 8, 2007

Related U.S. Application Data

(60) Provisional application No. 60/705,305, filed on Aug. 3, 2005.

(51) Int. Cl.
*A01K 67/027* (2006.01)
*C12N 5/06* (2006.01)
*C07K 16/18* (2006.01)

(52) U.S. Cl. .......................................... 800/14; 800/6
(58) Field of Classification Search .................. None
See application file for complete search history.

(56) References Cited

FOREIGN PATENT DOCUMENTS
WO          WO02/12437       *  2/2002
WO          WO 2004/037849     5/2004

OTHER PUBLICATIONS

Grillot, D., et al. "BCL-X Exhibits Regulated Expression During B Cell Development and Activation and Modulates Lymphocyte Survival in Transgenic Mice" Journal of Experimental Medicine, Tokyo, JP., vol. 183, Feb. 1996, pp. 381-391, XP002977276 ISSN: 0022-1007.
Guthrie, H et al., "Follicular Expression of a Human eta-Cell Leukaemia/Lymphoma-2 (Bcl-2) Transgene does not Decrease Atresia or Increase Ovulation Rate in Swine" Reproduction Fertility and Development, vol. 17, No. 4, Apr. 12, 2005, pp. 457-466 XP002407867 ISSN: 1031-3613.
Huang, J. et al., "BCL-XL Gene Transfer Protects the Heart Against Ischemia/Reperfusion Injury", Biochemical and Biophysical Research Communications, Academic Press Inc., Prlando, FL, US., vol. 311, No. 1, Nov. 7, 2003, pp. 64-70 XP004465104 ISSN: 0006-291X.
Janani, R. et al., Effect of a BCL-2 Transgene on Production and Localization of Precursor B Cells in Mouse Bone Marrow, Experimental Hematology (Charlottesville) vol. 26, No. 10, Sep. 1998, pp. 982-990 XP009074925 ISSN: 0301-472X.
Jasper, P. et al., "B Lymphocyte Development in rabbit Progenitor B Cells and Waning of B Lymphopoisis" Journal of Immunology, The Williams and Wilkins Co. Baltimore, US., vol. 171, No. 12, Dec. 2003, pp. 6372-6380 XP002368177 ISSN: 0022-1767.
Kuroiwa, Y et al., "Cloned Transchromosomic Calves Producing Human Immunoglobulin" Nature Biotechnlogy, Nature Publishing Group, New York, NY US, vol. 20, No. 9, Sep. 2002, pp. 889-894 XP002976595 ISSN: 1087-0156.
Shin Dong Hoon et al., "Localization of BCL-2 mRNA in the rabbit Central Nervous System" Nueroscience Letters, Limerick, IE, vol. 278, No. 1-2, Jan. 7, 2000, pp. 73-76 XP002390586 ISSN: 0304-3940.
Song et al., "Adenovirus-medaited bcL-2 Gene Transfer Inhibits Apoptosis and Promotes Survival of Allogenic Transplanted Hepatocytes" Surgery, C.V. Mosby Co., St. Louis, US., vol. 130, No. 3, Sep. 2001, pp. 502-512, 530 XP005156362 iSSN: 0039-6060.
McDonnell, T.J. et al., "bcl-2-Immunoglobulin Transgenic Mice Demonstrate Extended B Cell Survival and Follicular Lymphoproliferation", Cell, vol. 57, pp. 70-88 (Apr. 7, 1989).
McDonnell, T.J. et al., "Deregulated Bcl-2-Immunoglobulin Transgene Expands a Resting but Responsive Immunoglobulin M and D-Expressing B-Cell Population", Molecular and Cellular Biology, vol. 10, pp. 1901-1907 (May 1990).
A. Strasser, et al., "Abnormalities of the Immune system Induced by Dysregulated bcl-2 Expression in Transgenic Mice", The Walter and Eliza Hall Institute of Medical Research, Melbourne 3050, Australia, Current Topics in Immunology. 1990; vol. 166: pp. 175-181.
Takahashi, Yoshimasa et al., "Relaxed Negative Selection in Germinal Centers and Impaired Affinity Maturation in bcl-xL Transgenic Mice", J. Exp. Med @ The Rockefeller University Press, vol. 190, No. 3, pp. 399-409 (Aug. 2, 1999).
Smith, Kenneth et al., "bcl-2 transgene Expression Inhibits Apoptosis in the Germinal Center and Reveals Differences in the Selection of Memory B Cells and Bone Marrow Antibody-forming Cells.", J. Exp. Med @ The Rockefeller University Press, vol. 191, No. 3, pp. 475-484 (Feb. 7, 2000).
Knott, Christine et al., "Evaluation of Bcl-2/B Cell Transgenic Mice (B6) for Hybridoma Production", Hybridoma, vol. 15, No. 5, (1996).
A. Strasser, et al., "Enforced BCL2 Expression in B-lymphoid cells Prolongs Antibody Responses and Elicits Autoimmune Disease", Proc. Natl. Acad. Sci, USA, vol. 88, pp. 8661-8665, (Oct. 1991).

* cited by examiner

*Primary Examiner* — Scott Long
(74) *Attorney, Agent, or Firm* — Ginger R. Dreger; Arnold & Porter LLP

(57) ABSTRACT

The invention provides a novel approach to increase immunoglobulin expression in non-human transgenic animals. For instance, the invention provides a method to increase humanized immunoglobulin production in animals genetically engineered to express one or several human or humanized immunoglobulin transloci. This can be done by overexpressing the apoptosis inhibitor, i.e. a rabbit bcl-2, whose expression is driven by a B-cell specific promoter specifically in the B-cell of the animal, thereby enhancing the survival of B-cells. This invention further relates to a method for selectively enhancing the survival of exogenous B-cells, that is B-cells expressing any immunoglobulin transgene locus, over the survival of endogenous B-cells that do not express the transgene locus. Selectivity is achieved by expressing the apoptosis-inhibitor only within exogenous B-cells, that is, by coupling exogenous immunoglobulin expression with apoptosis inhibitor expression. This latter method allows for increased expression and production of the transgene encoded product(s) over the endogenously produced immunoglobulin of the transgenic animal. The invention also provides a novel apoptosis-inhibitor, rabbit bcl-2.

1 Claim, 7 Drawing Sheets

FIG. 2 (SEQ ID NO: 1)

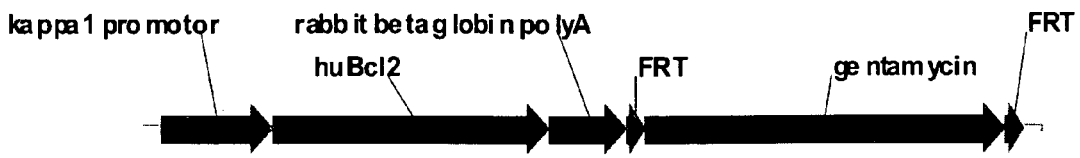

acataaatatactgtcttccaggatcttagagctcacctaaggaaacaagagttcatttgaagtttttaaagtgaacctcagtgactttggg
atgtgaactctccgagtagaagcatgcgcactgcaggtaaacttgtgcagccctggtctgagctggggcagctggagacacagcccc
tgggctgagttctgagctgccctgggcccttcagctgggcacagccctgccccgcccctgctcatttgcatgtccccagagcaccacc
cacctctctgggcatttaggagcaggctgctcccgcccccatgcaggaggcagtgccaggcaggacccagcatggcgcacgctggg
agaacagggtacgataaccgggagatagtgatgaagtacatccattataagctgtcgcagaggggctacgagtgggatgcgggaga
tgtgggcgccgcgcccccgggggccgcccccgcgccgggcatcttctcctcgcagcccgggcacacgccccatacagccgcatc
ccgggacccggtcgccaggacctcgccgctgcagaccccggctgccccggcgccgccgcggggcctgcgctcagcccggtgc
cacctgtggtccacctgaccctccgccaggccggcgacgacttctcccgccgctaccgccgcgacttcgccgagatgtccaggcag
ctgcacctgacgcccttcaccgcgcggggacgctttgccacggtggtggaggagctcttcagggacggggtgaactgggggagga
ttgtggccttctttgagttcggtggggtcatgtgtgtggagagcgtcaaccgggagatgtcgcccctggtggacaacatcgccctgtgg
atgactgagtacctgaaccggcacctgcacacctggatccaggataacggaggctgggatgcctttgtggaactgtacggccccagc
atgcggcctctgtttgatttctcctggctgtctctgaagactctgctcagtttggccctggtgggagcttgcatcaccctgggtgcctatctg
ggccacaagtgaatcttttcctctgccaaaaattatggggacatcatgaagccccttgagcatctgacttctggctaataaaggaaattt
atttcattgcaatagtgtgttggaattttttgtgtctctcactcggaaggacatatgggagggcaaatcatttaaaacatcagaatgagtatt
tggtttagagtttggcaacatatgccgaagttcctattccgaagttcctattctctagaaagtataggaacttctggagttgtagatcctctac
gccggacgcatcgtggccggcatcaccggctgaaggcacgaacccagttgacataagcctgttcggttcgtaaactgtaatgcaagt
agcgtatgcgctcacgcaactggtccagaaccttgaccgaacgcagcggtggtaacggcgcagtggcggttttcatggcttgttatga
ctgtttttttgtacagtctatgcctcgggcatccaagcagcaagcgcgttacgccgtgggtcgatgtttgatgttatggagcagcaacgat
gttacgcagcagcaacgatgttacgcagcagggcagtcgccctaaaacaaagttaggtggctcaagtatgggcatcattcgcacatgt
aggctcggccctgaccaagtcaaatccatgcgggctgctcttgatcttttcggtcgtgagttcggagacgtagccacctactcccaacat
cagccggactccgattacctcgggaacttgctccgtagtaagacattcatcgcgcttgctgccttcgaccaagaagcggttgttggcgc
tctcgcggcttacgttctgcccaggtttgagcagccgcgtagtgagatctatatctatgatctcgcagtctccggcgagcaccggaggc
agggcattgccaccgcgctcatcaatctcctcaagcatgaggccaacgcgcttggtgcttatgtgatctacgtgcaagcagattacggt
gacgatcccgcagtggctctctatacaaagttgggcatacgggaagaagtgatgcactttgatatcgacccaagtaccgccacctaac
aattcgttcaagccgaggttgtaacactggcagagcattacgctgacttgacgggacggcggcttttgttgaataaatcgaacttttgctg
agttgaaggatcagatcacgcatcttgaagttcctattccgaagttcctattctctagaaagtataggaacttcgattcacttttaagtagaa
attttataaaagtgggtaaatgagtaggttt

FIG. 3 (SEQ ID NO: 2)

DNA fragment encoding rabbit IgG M2-selfcleaving peptide F2A-human bcl2 fusion protein FRT rpsL-neo FRT

```
   1 GGTACCTGAA ACACACCATC GCTCCCGACT ACAGGAACAT GATCGGGCAG GGGGCCGTGA
  61 AACAGACTTT GAATTTTGAC CTTCTCAAGT TGGCGGGAGA CGTGGAGTCC AACCCAGGGC
 121 CCATGGCCCA CGCCGGGCGC ACTGGCTATG ATAATCGCGA AATTGTCATG AAGTATATTC
 181 ACTACAAGCT CTCTCAAAGA GGATACGAGT GGGATGCGGG GGACGTCGGC GCTGCCCCAC
 241 CTGGAGCTGC GCCGGCTCCA GGCATCTTTA GCAGCCAGCC GGGCCACACA CCTCACACCG
 301 CTGCCTCCAG GGATCCGGTG GCACGGACCA GCCCTCTGCA AACTCCCGCC GCCCCTGGGG
 361 CTGCAGCGGG TCCCGCCTTG TCCCCGGTGG CCCCTGTGGT GCACCTCACG CTGCGGCAGG
 421 CGGGCGACGA CTTCAGCAGG CGCTACAGAA GAGACTTTGC CGAAATGTCC CGCCAGCTCC
 481 ATCTGACCCC CTTCACCGCA CGAGGGAGGT TCGCCACCGT GGTCGAAGAA CTTTTCCGCG
 541 ACGGTGTGAA CTGGGGCCGC ATCGTTGCCT TTTTTGAGTT CGGGGGGGTT ATGTGCGTGG
 601 AATCAGTGAA CCGCGAAATG AGTCCCTTGG TCGACAACAT AGCTCTTTGG ATGACAGAGT
 661 ACCTGAACCG GCATCTGCAT ACTTGGATAC AGGACAACGG AGGATGGGAT GCTTTTGTTG
 721 AGCTGTACGG CCCATCAATG CGCCCCTTGT TCGACTTCAG CTGGTTGTCC CTGAAGACGC
 781 TCCTGAGCCT CGCTCTTGTG GGCGCCTGTA TCACTTTGGG CGCCTATCTC GGACATAAAT
 841 AAGAAGTTCC TATTCCGAAG TTCCTATTCT TCAAAAGGTA TAGGAACTTC GAATTCATTA
 901 CACCAGTGTC AGTAAGCGGG CAAAGTCGGT TAATGTCAGT TTCAAAACGT CCACCCATCA
 961 GGCCTGGTGA TGATGGCGGG ATCGTTGTAT ATTTCTTGAC ACCTTTTCGG CATCGCCCTA
1021 AAATTCGGCG TCCTCATATT GTGTGAGGAC GTTTTATTAC GTGTTTACGA AGCAAAAGCT
1081 AAAACCAGGA GCTATTTAAT GGCAACAGTT AACCAGCTGG TACGCAAACC ACGTGCTCGC
1141 AAAGTTGCGA AAAGCAACGT GCCTGCGCTG GAAGCATGCC CGCAAAAACG TGGCGTATGT
1201 ACTCGTGTAT ATACTACCAC TCCTAAAAAA CCGAACTCCG CGCTGCGTAA AGTATGCCGT
1261 GTTCGTCTGA CTAACGGTTT CGAAGTGACT TCCTACATCG GTGGTGAAGG TCACAACCTG
1321 CAGGAGCACT CCGTGATCCT GATCCGTGGC GGTCGTGTTA AAGACCTCCC GGGTGTTCGT
1381 TACCACACCG TACGTGGTGC GCTTGACTGC TCCGGCGTTA AAGACCGTAA GCAGGCTCGT
1441 TCCAAGTATG GCGTGAAGCG TCCTAAGGCT TAAGGAGGAC AATCATGATT GAACAAGATG
1501 GATTGCACGC AGGTTCTCCG GCCGCTTGGG TGGAGAGGCT ATTCGGCTAT GACTGGGCAC
1561 AACAGACAAT CGGCTGCTCT GATGCCGCCG TGTTCCGGCT GTCAGCGCAG GGGCGCCCGG
1621 TTCTTTTTGT CAAGACCGAC CTGTCCGGTG CCCTGAATGA ACTGCAGGAC GAGGCAGCGC
1681 GGCTATCGTG GCTGGCCACG ACGGGCGTTC CTTGCGCAGC TGTGCTCGAC GTTGTCACTG
1741 AAGCGGGAAG GGACTGGCTG CTATTGGGCG AAGTGCCGGG GCAGGATCTC CTGTCATCTC
1801 ACCTTGCTCC TGCCGAGAAA GTATCCATCA TGGCTGATGC AATGCGGCGG CTGCATACGC
1861 TTGATCCGGC TACCTGCCCA TTCGACCACC AAGCGAAACA TCGCATCGAG CGAGCACGTA
1921 CTCGGATGGA AGCCGGTCTT GTCGATCAGG ATGATCTGGA CGAAGAGCAT CAGGGGCTCG
1981 CGCCAGCCGA ACTGTTCGCC AGGCTCAAGG CGCGCATGCC CGACGGCGAG GATCTCGTCG
2041 TGACCCATGG CGATGCCTGC TTGCCGAATA TCATGGTGGA AAATGGCCGC TTTTCTGGAT
2101 TCATCGACTG TGGCCGGCTG GGTGTGGCGG ACCGCTATCA GGACATAGCG TTGGCTACCC
2161 GTGATATTGC TGAAGAGCTT GGCGGCGAAT GGGCTGACCG CTTCCTCGTG CTTTACGGTA
2221 TCGCCGCTCC CGATTCGCAG CGCATCGCCT TCTATCGCCT TCTTGACGAG TTCTTCTGAG
2281 AAGTTCCTAT TCCGAAGTTC CTATTCTTCA AAAGGTATAG GAACTTCGCC CTTCGTTCTC
2341 ACAGCCTGCC TCCCTGGCCA GCAGGAGCCC CCGCCTCCTC GAG
```

FIG. 4: (SEQ ID NO: 3)

rpsL-neo flanked with FRT and FRT2 sites

```
   1 CGTCCATTCC CAACACATGA ACAGCATCTC ACGCCACCTC TGTTGCCTGC GAAGTTCCTA
  61 TTCCGAAGTT CCTATTCTCT ACTTAGTATA GGAACTTCAT TACACCAGTG TCAGTAAGCG
 121 GGCAAAGTCG GTTAATGTCA GTTTCAAAAC GTCCACCCAT CAGGCCTGGT GATGATGGCG
 181 GGATCGTTGT ATATTTCTTG ACACCTTTTC GGCATCGCCC TAAAATTCGG CGTCCTCATA
 241 TTGTGTGAGG ACGTTTTATT ACGTGTTTAC GAAGCAAAAG CTAAAACCAG GAGCTATTTA
 301 ATGGCAACAG TTAACCAGCT GGTACGCAAA CCACGTGCTC GCAAAGTTGC GAAAAGCAAC
 361 GTGCCTGCGC TGGAAGCATG CCCGCAAAAA CGTGGCGTAT GTACTCGTGT ATATACTACC
 421 ACTCCTAAAA AACCGAACTC CGCGCTGCGT AAAGTATGCC GTGTTCGTCT GACTAACGGT
 481 TTCGAAGTGA CTTCCTACAT CGGTGGTGAA GGTCACAACC TGCAGGAGCA CTCCGTGATC
 541 CTGATCCGTG GCGGTCGTGT TAAAGACCTC CCGGGTGTTC GTTACCACAC CGTACGTGGT
 601 GCGCTTGACT GCTCCGGCGT TAAAGACCGT AAGCAGGCTC GTTCCAAGTA TGGCGTGAAG
 661 CGTCCTAAGG CTTAAGGAGG ACAATCATGA TTGAACAAGA TGGATTGCAC GCAGGTTCTC
 721 CGGCCGCTTG GGTGGAGAGG CTATTCGGCT ATGACTGGGC ACAACAGACA ATCGGCTGCT
 781 CTGATGCCGC CGTGTTCCGG CTGTCAGCGC AGGGGCGCCC GGTTCTTTTT GTCAAGACCG
 841 ACCTGTCCGG TGCCCTGAAT GAACTGCAGG ACGAGGCAGC GCGGCTATCG TGGCTGGCCA
 901 CGACGGGCGT TCCTTGCGCA GCTGTGCTCG ACGTTGTCAC TGAAGCGGGA AGGGACTGGC
 961 TGCTATTGGG CGAAGTGCCG GGGCAGGATC TCCTGTCATC TCACCTTGCT CCTGCCGAGA
1021 AAGTATCCAT CATGGCTGAT GCAATGCGGC GGCTGCATAC GCTTGATCCG GCTACCTGCC
1081 CATTCGACCA CCAAGCGAAA CATCGCATCG AGCGAGCACG TACTCGGATG GAAGCCGGTC
1141 TTGTCGATCA GGATGATCTG GACGAAGAGC ATCAGGGGCT CGCGCCAGCC GAACTGTTCG
1201 CCAGGCTCAA GGCGCGCATG CCCGACGGCG AGGATCTCGT CGTGACCCAT GGCGATGCCT
1261 GCTTGCCGAA TATCATGGTG GAAAATGGCC GCTTTTCTGG ATTCATCGAC TGTGGCCGGC
1321 TGGGTGTGGC GGACCGCTAT CAGGACATAG CGTTGGCTAC CCGTGATATT GCTGAAGAGC
1381 TTGGCGGCGA ATGGGCTGAC CGCTTCCTCG TGCTTTACGG TATCGCCGCT CCCGATTCGC
1441 AGCGCATCGC CTTCTATCGC CTTCTTGACG AGTTCTTCTG AGAAGTTCCT ATTCCGAAGT
1501 TCCTATTCTC TAGAAAGTAT AGGAACTTCC CTGAGAAGGA TGTCGGAGGC AAGAGACAA
1561 GCCCGCCGTG GCCCTGCTC
```

FIG. 5: (SEQ ID NO: 4)

DNA fragment encoding rabbit IgM-M2-selfcleaving peptide F2A-codon optimized human bcl2 fusion protein flanked with FRT and FRT2 sites

```
   1 GAATTCGAAG TTCCTATTCC GAAGTTCCTA TTCTCTACTT AGTATAGGAA CTTCAGGTGA
  61 AGCAGACTTT GAATTTTGAC CTTCTCAAGT TGGCGGGAGA CGTGGAGTCC AACCCAGGGC
 121 CCATGGCCCA CGCCGGGCGC ACTGGCTATG ATAATCGCGA AATTGTCATG AAGTATATTC
 181 ACTACAAGCT CTCTCAAAGA GGATACGAGT GGGATGCGGG GGACGTCGGC GCAGCTCCAC
 241 CTGGAGCTGC GCCGGCCCCT GGCATCTTTA GCAGCCAGCC GGGCCACACA CCTCACACCG
 301 CTGCCTCCAG GGATCCGGTG GCACGGACCA GCCCTCTGCA AACTCCCGCC GCCCCTGGGG
 361 CTGCAGCGGG TCCCGCCTTG TCCCCGGTGC CCCCTGTGGT GCACCTCACG CTGCGGCAGG
 421 CGGGCGACGA CTTCAGCAGG CGCTACAGAA GAGACTTTGC CGAAATGTCC CGCCAGCTCC
 481 ATCTGACCCC CTTCACCGCA CGAGGGAGGT TCGCCACCGT GGTCGAAGAA CTTTTCCGCG
 541 ACGGTGTGAA CTGGGGCCGC ATCGTTGCCT TTTTTGAGTT CGGGGGGGTT ATGTGCGTGG
 601 AATCAGTGAA CCGCGAAATG AGTCCCTTGG TCGACAACAT AGCTCTTTGG ATGACAGAGT
 661 ACCTGAACCG GCATCTGCAT ACTTGGATAC AGGACAACGG AGGATGGGAT GCTTTTGTTG
 721 AGCTGTACGG CCCCATCAATG CGCCCCTTGT TCGACTTCAG CTGGTTGTCC CTGAAGACGC
 781 TCCTGAGCCT CGCTCTTGTG GGCGCCTGTA TCACTTTGGG CGCCTATCTC GGACATAAAT
 841 AAGAAGTTCC TATTCCGAAG TTCCTATTCT CTAGAAAGTA TAGGAACTTC CTCGAGGAAT
 901 TC
```

FIG. 6: (SEQ ID NO: 5)

MAHAGRTGYDNREIVMKYIHYKLSQRGYEWDAGDAGAASAPGVFSSQPAPAAPRDPAARTSP
PPPPAAAGPALSPVPPVVHLTLRQAGDDFSRRYRRDFAEMSSQLHLTPFTARGRFATVVEEL
FRDGVNWGRIVAFFEFGGVMCVESVNREMSPLVDNIALWMTEYLNRHLHTWIQDNGGWDAFV
ELYGPSVRPLSDFSWVSLKTLFSLALIGACITLGAYLGHK*

FIG. 7 (SEQ ID NO: 6)

DNA fragment encoding rabbit IgM-M2-selfcleaving peptide F2A-codon optimized human bcl2 fusion protein

```
aggtgaagcagactttgaattttgaccttctcaagttggcgggagacgtggagtccaaccca
gggcccatggcccacgccgggcgcactggctatgataatcgcgaaattgtcatgaagtatat
tcactacaagctctctcaaagaggatacgagtgggatgcggggacgtcggcgcagctccac
ctggagctgcgccggccctggcatctttagcagccagccgggccacacacctcacaccgct
gcctccagggatccggtggcacggaccagccctctgcaaactcccgccgccctggggctgc
agcgggtcccgccttgtccccggtgcccctgtggtgcacctcacgctgcggcaggcgggcg
acgacttcagcaggcgctacagaagagactttgccgaaatgtcccgccagctccatctgacc
cccttcaccgcacgagggaggttcgccaccgtggtcgaagaacttttccgcgacggtgtgaa
ctggggccgcatcgttgcctttttgagttcgggggggttatgtgcgtggaatcagtgaacc
gcgaaatgagtcccttggtcgacaacatagctctttggatgacagagtacctgaaccggcat
ctgcatacttggatacaggacaacggaggatgggatgcttttgttgagctgtacggcccatc
aatgcgccccttgttcgacttcagctggttgtccctgaagacgctcctgagcctcgctcttg
tgggcgcctgtatcactttgggcgcctatctcggacataaataa
```

FIG. 8 (SEQ ID NO: 7)

DNA fragment encoding rabbit IgM-M2-selfcleaving peptide F2A-human bcl2 fusion protein

```
aggtgaagcagactttgaattttgaccttctcaagttggcgggagacgtggagtccaaccca
gggcccatggcgcacgctgggagaacagggtacgataaccgggagatagtgatgaagtacat
ccattataagctgtcgcagaggggctacgagtgggatgcgggagatgtgggcgccgcgcccc
cgggggccgcccccgcgccgggcatcttctcctcgcagcccgggcacacgcccatacagcc
gcatcccgggacccggtcgccaggacctcgccgctgcagacccggctgccccggcgccgc
cgcggggcctgcgctcagcccggtgccacctgtggtccacctgaccctccgccaggccggcg
acgacttctcccgccgctaccgccgcgacttcgccgagatgtccaggcagctgcacctgacg
cccttcaccgcgcggggacgctttgccacggtggtggaggagctcttcagggacggggtgaa
ctgggggaggattgtggccttctttgagttcggtggggtcatgtgtgtggagagcgtcaacc
gggagatgtcgccctggtggacaacatcgccctgtggatgactgagtacctgaaccggcac
ctgcacacctggatccaggataacggaggctgggatgcctttgtggaactgtacggccccag
catgcggcctctgtttgatttctcctggctgtctctgaagactctgctcagtttggccctgg
tgggagcttgcatcaccctgggtgcctatctgggccacaagtga
```

FIG. 9 (SEQ ID NO: 8)

DNA fragment encoding an IgG-M2-selfcleaving peptide F2A-codon optimized human bcl2 fusion protein

```
Aggtgaagtggatcttctcgtccgtggtggagctgaaacacaccatcgctcccgactacagg
aacatgatcgggcagggggccgtgaaacagactttgaattttgaccttctcaagttggcggg
agacgtggagtccaacccagggcccatggcccacgccgggcgcactggctatgataatcgcg
aaattgtcatgaagtatattcactacaagctctctcaaagaggatacgagtgggatgcgggg
gacgtcggcgctgccccacctggagctgcgccggctccaggcatctttagcagccagccggg
ccacacacctcacaccgctgcctccagggatccggtggcacggaccagccctctgcaaactc
ccgccgccctggggctgcagcgggtcccgccttgtcccggtgcccctgtggtgcacctc
acgctgcggcaggcgggcgacgacttcagcaggcgctacagaagagactttgccgaaatgtc
ccgccagctccatctgaccccttcaccgcacgagggaggttcgccaccgtggtcgaagaac
ttttccgcgacggtgtgaactggggccgcatcgttgcctttttgagttcggggggggttatg
tgcgtggaatcagtgaaccgcgaaatgagtcccttggtcgacaacatagctctttggatgac
agagtacctgaaccggcatctgcatacttggatacaggacaacggaggatgggatgcttttg
ttgagctgtacggcccatcaatgcgccccttgttcgacttcagctggttgtccctgaagacg
ctcctgagcctcgctcttgtgggcgcctgtcactttgggcgcctatctcggacataaata
a
```

FIG. 10 (SEQ ID NO: 9)

DNA fragment encoding rabbit IgM-M2-furin cleavage site-self cleaving peptide F2A-human bcl2 fusion protein

```
aggtgaagcgagcaaagcgaccggtgaaacagactttgaattttgaccttctcaagttggcg
ggagacgtggagtccaacccagggcccatggcgcacgctgggagaacagggtacgataaccg
ggagatagtgatgaagtacatccattataagctgtcgcagaggggctacgagtgggatgcgg
gagatgtgggcgccgcgccccggggccgccccgcgccgggcatcttctcctcgcagccc
gggcacacgccccatacagccgcatcccgggaccggtcgccaggacctcgccgctgcagac
cccggctgccccggcgccgccgcggggcctgcgctcagcccggtgccacctgtggtccacc
tgaccctcgccaggccggcgacgacttctcccgccgctaccgccgcgacttcgccgagatg
tccaggcagctgcacctgacgcccttcaccgcgcggggacgctttgccacggtggtggagga
gctcttcagggacggggtgaactgggggaggattgtggccttctttgagttcggtggggtca
tgtgtgtggagagcgtcaacgggagatgtcgccctggtggacaacatcgccctgtggatg
actgagtacctgaaccggcacctgcacacctggatccaggataacggaggctgggatgcctt
tgtggaactgtacggccccagcatgcggcctctgtttgatttctcctggctgtctctgaaga
ctctgctcagtttggccctggtgggagcttgcatcaccctgggtgcctatctgggccacaag
tga
```

FIG. 11 (SEQ ID NO: 10)

DNA fragment encoding rabbit IgG-M2-furin cleavage site-self cleaving peptide F2A-codon optimized human bcl2 fusion protein

```
aggtgaagtggatcttctcgtccgtggtggagctgaaacacaccatcgctcccgactacagg
aacatgatcgggcaggggcccgagcaaagcgaccggtgaaacagactttgaattttgacct
tctcaagttggcggggagacgtggagtccaacccagggcccatggcccacgccgggcgcactg
gctatgataatcgcgaaattgtcatgaagtatattcactacaagctctctcaaagaggatac
gagtgggatgcggggggacgtcggcgctgccccacctggagctgcgccggctccaggcatctt
tagcagccagccgggccacacacctcacaccgctgcctccagggatccggtggcacggacca
gccctctgcaaactcccgccgccctggggctgcagcgggtcccgccttgtccccggtgccc
cctgtggtgcacctcacgctgcggcaggcgggcgacgacttcagcaggcgctacagaagaga
ctttgccgaaatgtcccgccagctccatctgacccccttcaccgcacgagggaggttcgcca
ccgtggtcgaagaacttttccgcgacggtgtgaactggggccgcatcgttgcctttttgag
ttcgggggggttatgtgcgtggaatcagtgaaccgcgaaatgagtcccttggtcgacaacat
agctctttggatgacagagtacctgaaccggcatctgcatacttggatacaggacaacggag
gatgggatgcttttgttgagctgtacggcccatcaatgcgcccttgttcgacttcagctgg
ttgtccctgaagacgctcctgagcctcgctcttgtgggcgcctgtatcactttgggcgccta
tctcggacataaataa
```

SUPPRESSION OF B-CELL APOPTOSIS IN TRANSGENIC ANIMALS EXPRESSING HUMANIZED IMMUNOGLOBULIN

CROSS-REFERENCE TO RELATED APPLICATIONS

This is a non-provisional application filed under 37 CFR 1.53(b), claiming priority under U.S.C. Section 19(e) to U.S. Provisional Patent Application Ser. No. 60/705,305 filed Aug. 3, 2005.

FIELD OF THE INVENTION

This invention relates to methods for enhancing the survival of B-cells in animals undergoing short-term lymphopoiesis. This invention further relates to methods for enhancing the survival of B-cells of transgenic animals expressing an exogenous immunoglobulin or immunoglobulin chain transgene locus for increasing the production of immunoglobulins. This invention further relates to a method for selectively enhancing the survival of exogenous B-cells expressing any immunoglobulin transgene locus over endogenous B-cells that do not express the transgene locus by selectively expressing any apoptosis-inhibitor only within exogenous B-cells expressing the transgene-encoded immunoglobulin, but not within B-cells expressing endogenous immunoglobulin. This method allows for the increased expression and production of the transgene encoded product(s) over the endogenously produced immunoglobulin of the transgenic animal. The invention also provides a novel apoptosis-inhibitor, rabbit bcl-2.

BACKGROUND ART

The generation of mice expressing human-mouse chimeric antibodies has been described by Pluschke et al., *Journal of Immunological Methods* 215: 27-37 (1998). The generation of mice expressing human immunoglobulin polypeptides has been described by Neuberger et al., *Nature* 338: 350-2 (1989); Lonberg et al., *Int. Rev. Immunol.* 13(1):65-93 (1995); and Bruggemann et al., *Curr. Opin. Biotechnol.*, 8(4): 455-8 (1997). Generation of transgenic mice using a BAC clone has been described by Yang et al., *Nat. Biotechnol.* 15: 859-65 (1997). The generation of cows expressing human antibodies has been described by Kuroiwa et al., *Nature Biotech* 20(9): 889-894 (2002).

Transgenesis in animals has been described by Wall R J, *Theriogenology* 57(1): 189-201 (2002). The generation of transgenic rabbits has been described by Fan, J. et al., *Pathol Int.* 49: 583-94 (1999); and Brem et al., *Mol. Reprod. Dev.* 44: 56-62 (1996). The production of transgenic chicken has been described by Etches et al., *Methods in Molecular Biology* 62: 433-450 (1997); and Pain et al., *Cells Tissues Organs* 165(3-4): 212-9 (1999); and Sherman et al., *Nature Biotech* 16:1050-1053 (1998).

Rabbits with impaired immunoglobulin expression have been described by Chen et al., *J. Immunol.* 150:2783-2793 (1993); and Lamoyi E, and Mage R G., *J. Exp. Med.* 162: 1149-1160 (1985). A gamma-globulinemic chicken has been described by Frommel et al., *J. Immunol.* 105(1): 1-6 (1970); and Benedict et al., *Adv. Exp. Med. Biol.* 88(2): 197-205 (1977).

The cloning of animals from cells has been described by T. Wakayama et al., *Nature* 394:369-374 (1998); J. B. Cibelli et al., *Science* 280:1256-1258 (1998); J. B. Cibelli et al., *Nature Biotechnology* 16:642-646 (1998); A. E. Schnieke et al., *Science* 278: 2130-2133 (1997); and K. H. Campbell et al., *Nature* 380: 64-66 (1996). Nuclear transfer cloning of rabbits has been described by Stice et al., *Biology of Reproduction* 39: 657-664 (1988); Challah-Jacques et al., *Cloning and Stem Cells* 8(4):295-299 (2003).

The production of non-human transgenic animals expressing human(ized) immunoglobulin transloci and the production of antibodies from such transgenic animals have been described in detail in PCT Publication Nos. WO 92/03918, WO 02/12437, and in U.S. Pat. Nos. 5,545,807, 5,814,318; and 5,570,429. Homologous recombination for chimeric mammalian hosts is exemplified in U.S. Pat. No. 5,416,260. A method for introducing DNA into an embryo is described in U.S. Pat. No. 5,567,607. Maintenance and expansion of embryonic stem cells is described in U.S. Pat. No. 5,453,357.

The cleavage activities of viral proteins containing 2A peptide sequences have been described by Palmenberg et al., *Virology* 190:754-762 (1992); Ryan et al., *J Gen Virol* 72:2727-2732 (1991); Donnelly et al., *J Gen Virol* 82:1027-1041 (2001); Donnelly et al., *J Gen Virol* 82:1013-1025 (2001); Szymaczak et al., *Nature Biotech* 22(5):589-594 (2004).

So far, studies of the relative contribution of cell survival mechanisms regulated by the apoptosis inhibitor bcl-2, have been performed mainly in mice. The effect of bcl-2 expression on cell survival has been described by McDonnell et al., *Cell*, 57:79-88, (1989); Strasser et al., *Current Topics in Microbiology and Immunology*, 166:175-181, (1990); Knott et al., *Hybridoma*, 15 (5):365-371, (1996); Smith et al., *J. Exp. Med.*, 191(3):475-784 (2000); Strasser et al., *PNAS*, 88:8661-8665, (1991) and Kumar et al., *Immunology Letters*, 65:153-159, (1999). The effect of the apoptosis inhibitor bcl-$x_L$ expression on cell survival has been described by Takahashi et al., *J. Exp. Med.*, 190(3): 399-409 (1999).

Mechanisms of B-cell development such as continuous and short-term B lymphopoiesis have been reviewed in Lanning D, Osborne B A, Knight, K L., Immunoglobulin genes and generation of antibody repertoires in higher vertebrates: a key role of GALT. Molecular Biology of B-cells. Alt F. W., Honjo T, Nueberger, M. S., Eds. Elsevier London, p 443 (2004); and Flajnik M. F., Comparative analysis of immunoglobulin genes: surprises and portents. *Nat. Rev. Immunol.* 2:688, (2002).

Since production of antibodies in larger transgenic animals like rabbits, chickens, sheep and cows is favored from the standpoint of antibody yield, creation of larger founder animals with B-cell apoptosis inhibition expressing higher amounts of transgene-encoded products is highly desirable. However, B-cell development differs significantly in species undergoing short-term lymphopoiesis (like rabbits, chickens, sheep and cows) relative to animals characterized by continuous B lymphopoiesis (like mice). Thus, it is unclear if apoptosis inhibitors can be used with the same success in animals undergoing short-term lymphopoiesis as in the more extensively studied animals with continuous B lymphopoiesis, or, what the impact of apoptosis inhibitors on antibody production and/or antibody affinities will be.

SUMMARY OF THE INVENTION

In one aspect, the invention provides a polypeptide comprising a novel apoptosis-inhibitor polypeptide, namely, the rabbit bcl-2 polypeptide of SEQ ID NO: 5. In a particular embodiment, the invention provides a chimeric molecule comprising the rabbit bcl-2 polypeptide of SEQ ID NO: 5 fused to a heterologous amino acid sequence. In a further embodiment, the heterologous amino acid sequence is an epitope sequence. In another embodiment, the heterologous amino acid sequence is an immunoglobulin sequence. In yet another embodiment, the immunoglobulin sequence is an Fc region of an immunoglobulin. The present invention also provides a nucleotide sequences encoding the rabbit bcl-2 polypeptide of SEQ ID NO: 5. In one aspect, the invention provides a vector, expression cassette or transgenic expression construct comprising the nucleic acid molecule that encodes the rabbit bcl-2 polypeptide. In another aspect, the invention provides an isolated host cell transformed with the nucleic acid sequences encoding the rabbit bcl-2 polypeptide of SEQ ID NO: 5. In a further aspect, the invention provides an isolated host cell transformed with the vector, expression cassette or transgenic expression construct comprising the nucleic acid molecule that encodes the rabbit bcl-2 polypeptide.

In some aspects, any apoptosis inhibitor gene can be used, for example, an apoptosis inhibitor selected from the group consisting of bcl-2, caspase-9-DN mutants, baculovirus p35, caspase-9S, crmA, z-VAD-fmk, z-DEVD-fmk, B-D-fmk, z-YVAD-fmk, Bcl-$x_L$, Mcl-1, XIAP, TIAP, KIAP, NAIP, cIAP1, cIAP2, API1, API2, API3, API4, HIAP1, HIAP2, MIHA, MIHB, MIHC, ILP, ILP-2, TLAP, survivin, livin, apollon, BRUCE, MLIAP, SODD and FLIP and variants thereof. In some specific embodiments, the apoptosis inhibitor gene may be a mammalian bcl-2 gene. In some preferred embodiments, the mammalian bcl-2 gene is selected from the group consisting of human bcl-2, mouse bcl-2 and rabbit bcl-2 of SEQ ID NO: 6. In a preferred embodiment, the bcl-2 is the rabbit bcl-2 of SEQ ID NO: 5.

In one aspect, the invention provides a transgenic expression construct comprising a nucleic acid molecule that encodes an apoptosis inhibitor driven by a B-cell specific promoter/enhancer and thus, is specifically expressed in B-cells.

In another aspect, the invention provides a transgenic expression construct comprising a transgene encoding a fusion-protein comprising polypeptide sequences in the following order: a) an immunoglobulin or immunoglobulin chain; b) a self-cleaving peptide; c) an apoptosis inhibitor; and optionally, d) a protease cleavage site between a) and b).

The present invention further provides a method for enhancing the expression of an immunoglobulin or immunoglobulin chain in a transgenic animal undergoing short-term lymphopoiesis, comprising introducing into the transgenic animal undergoing short-term lymphopoiesis at least one transgene construct comprising an apoptosis-inhibitor transgene driven by a B-cell specific promoter/enhancer whereby apoptosis of the B-cells carrying said transgene construct is inhibited and production of the immunoglobulin or immunoglobulin chain is enhanced.

In a further aspect, the present invention provides a method for enhancing the expression of an immunoglobulin or immunoglobulin chain in the short-term lymphopoietic transgenic animal that further comprises introducing into the transgenic animal at least one more transgene encoding for an exogenous immunoglobulin or immunoglobulin chain transgene locus. In this method, the two transgenes can both be present on the same or on different transgenic expression vectors. In the latter case, the different transgenic expression vectors can be introduced into the transgenic animal either at the same time or sequentially.

The present invention also provides a method for selectively enhancing the expression of an exogenous immunoglobulin or immunoglobulin chain within an exogenous B-cell of a non-human transgenic animal, comprising introducing into the animal, a transgene construct encoding a fusion-protein comprising polypeptide sequences in the following order: a) an immunoglobulin or immunoglobulin chain; b) a self-cleaving peptide; c) an apoptosis inhibitor, and, optionally; d) a protease cleavage site between a) and b), whereby survival of the exogenous B cell and exogenous immunoglobulin production are enhanced.

In any aspect, the protease cleavage site used in any of the transgenic constructs or methods described above, is selected from the group consisting of sites for aspartic proteases, cysteine proteases, metalloproteases, serine proteases and threonine proteases. In preferred embodiments, the furin cleavage site is used.

In all aspects of the invention, the B-cell specific promoter/enhancer may be selected from the group consisting of promoters/enhancers of CD19, CD20, CD21, CD22, CD23, CD24, CD40, CD72, Blimp-1, CD79b, mb-1, tyrosine kinase blk, VpreB, immunoglobulin heavy chain, immunoglobulin kappa light chain, immunoglobulin lambda-light chain and immunoglobulin J-chain, or modifications thereof. In specific embodiments, the B-cell specific promoter/enhancer is the immunoglobulin kappa light chain gene promoter or a modification thereof.

In all aspects of the invention, the preferred exogenous immunoglobulin(s)/immunoglobulin chain transgene locus is the human/humanized immunoglobulin heavy and/or light chain sequence.

In all aspects of the invention, the self-cleaving peptide of the invention can be obtained from viral 2A/2B or 2A-like/2B sequences. Thus, the virus may be selected from the group consisting of the picornaviridae virus family, the equine rhinitis A (ERAV) virus family, the picornavirus-like insect virus family and from the type C rotavirus family. The virus may also be selected from the group consisting of the foot and mouth disease virus (FMDV), the equine rhinitis A (ERAV) virus, and the *Thosea asigna* virus (TaV).

In a further aspect of the invention, the invention relates to non-human transgenic animals comprising the transgenic constructs described above. For instance, the apoptosis inhibitor transgenes are preferably introduced into animals undergoing short-term lymphopoiesis. These include, but are not limited to, rabbits, birds, chickens, sheep, goats, cows, swine, horses and donkeys. These short-term lymphopoietic animals may further comprise transgenes, for instance, encoding an immunoglobulin(s)/immunoglobulin chain transgene. On the other hand, the fusion-protein encoding transgenes can be introduced into any non-human animal.

Thus, in most aspects of the invention, unless specified, non-human animals are selected from the group consisting of rodents (e.g. mice, rats), rabbits, birds (e.g. chickens, turkeys, ducks, geese, etc.), cows, pigs, sheep, goats, horses, donkeys and other farm animals. In some aspects of the invention, the non-human transgenic animal can either substantially stops antibody diversification by gene rearrangement early in life or substantially stops antibody diversification within the first month of its life. In a specific embodiment, the non-human transgenic animal is the rabbit.

BRIEF DESCRIPTION OF DRAWINGS

FIG. 2: SEQ ID NO: 1; A synthetic human bcl-2 apoptosis inhibition vector under the control of the kappa 1 B cell specific promoter.

FIG. 3: SEQ ID NO: 2; DNA fragment encoding rabbit IgG M2-self cleaving peptide F2A-human bcl2 fusion protein FRT rpsL-neo FRT.

FIG. 4: SEQ ID NO: 3; DNA fragment encoding rpsL-neo flanked with FRT and FRT2 sites.

FIG. 5: SEQ ID NO: 4; DNA fragment encoding rabbit IgM-M2-self cleaving peptide F2A-codon optimized human bcl2 fusion protein flanked with FRT and FRT2 sites.

FIG. 6: SEQ ID NO: 5; The rabbit bcl-2 polypeptide sequence.

FIG. 7: SEQ ID NO: 6; DNA fragment encoding rabbit IgM-M2-self cleaving peptide F2A-codon optimized human bcl2 fusion protein.

FIG. 8: SEQ ID NO: 7; DNA fragment encoding rabbit IgM-M2-self cleaving peptide F2A-human bcl2 fusion protein FIG. 9: SEQ ID NO: 8; DNA fragment encoding an IgG-M2-self cleaving peptide F2A-codon optimized human bcl2 fusion protein FIG. 10: SEQ ID NO: 9; DNA fragment encoding rabbit IgM-M2-furin cleavage site-self cleaving peptide F2A-human bcl2 fusion protein FIG. 11: SEQ ID NO: 10; DNA fragment encoding rabbit IgG-M2-furin cleavage site-self cleaving peptide F2A-codon optimized human bcl2 fusion protein

DETAILED DESCRIPTION OF THE INVENTION

Definitions

Figure 1:
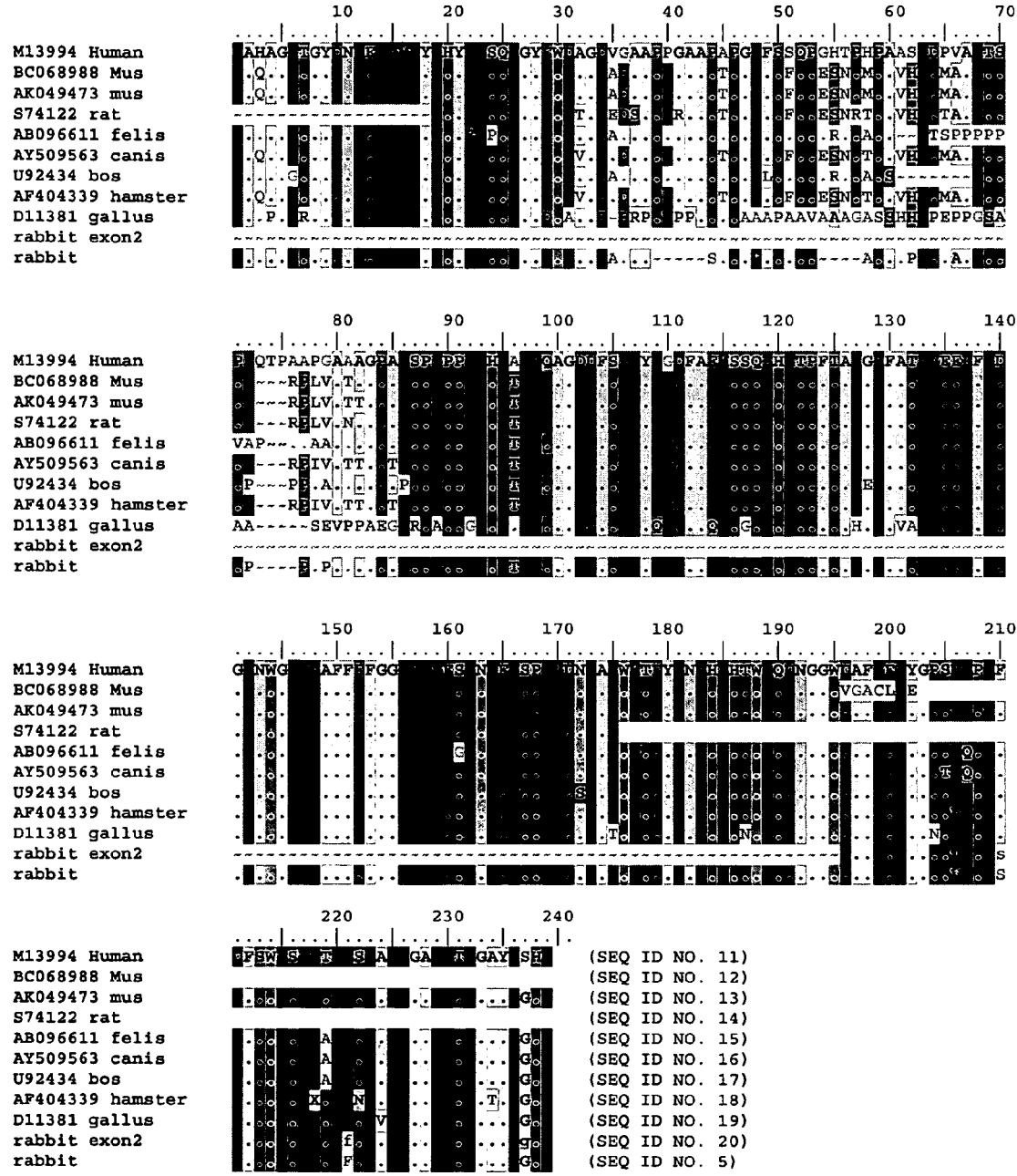
FIG. 1 shows an amino acid alignment of the rabbit polypeptide sequence (SEQ ID NO: 5) with other bcl-2 molecules derived from other species (SEQ ID NOS: 11-20).

Unless defined otherwise, technical and scientific terms used herein have the same meaning as commonly understood by one of ordinary skill in the art to which this invention belongs. Singleton et al., *Dictionary of Microbiology and Molecular Biology* 2nd ed., J. Wiley & Sons (New York, N.Y. 1994), and March, *Advanced Organic Chemistry Reactions, Mechanisms and Structure* 4th ed., John Wiley & Sons (New York, N.Y. 1992), provide one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described. For purposes of the present invention, the following terms are defined below.

"B-cells" are defined as B-lineage cells that are capable of undergoing rearrangement of immunoglobulin gene segments and expressing immunoglobulin genes at some stage in their life cycle. These cells include, but are not limited to, early pro-B-cells, late pro-B-cells, large pre-B-cells, small pre-B-cells, immature B-cells, mature B-cells, memory B-cells, plasma cells, etc.

"Apoptosis-inhibitors" refer to a molecule or substance the presence or expression of which provides a reduction of apoptosis in target cells, regardless of the underlying mechanism. Preferably, the apoptosis-inhibitor reduces apoptosis of a target cell by at least about 50%, or at least about 60%, or at least about 70%, or at least about 75%, or at least about 80%, or at least about 85%, or at least about 90%, or at least about 95% relative to apoptosis in the absence of the inhibitor.

The term "human Ig gene translocus or locus or segment" as used herein includes both naturally occurring sequences of a human Ig gene locus or a segment thereof, degenerate forms of naturally occurring sequences of a human Ig gene locus or segments thereof, as well as synthetic sequences that encode a polypeptide sequence substantially identical to a polypeptide encoded by a naturally occurring sequence of a human Ig gene locus or a segment thereof. In this context, by "substantially" is meant the degree of amino acid sequence identity is preferably at least about 85%-95%, or more preferably at least about 90%-95%, or even more preferably at least about 95%, or most preferably at least about 98%. In a particular embodiment, the human Ig gene segment renders the immunoglobulin molecule non-immunogenic in humans. Here, the terms "human or humanized immunoglobulin (Ig) heavy and/or light chain locus" or "human or human(ized) Ig locus" are used interchangeably.

The terms "human antibody" and "human immunoglobulin" are used herein to refer to antibodies and immunoglobulin molecules comprising fully human sequences.

The terms "humanized antibody" and "humanized immunoglobulin," as used herein, mean an immunoglobulin molecule comprising at least a portion of a human immunoglobulin polypeptide sequence (or a polypeptide sequence encoded by a human immunoglobulin gene segment). The humanized immunoglobulin molecules of the present invention can be isolated from a transgenic non-human animal engineered to produce humanized immunoglobulin molecules. Such humanized immunoglobulin molecules are less immunogenic to primates, especially humans, relative to non-humanized immunoglobulin molecules prepared from the animal or prepared from cells derived from the animal. Humanized immunoglobulins or antibodies include immunoglobulins (Igs) and antibodies that are further diversified through gene conversion and somatic hypermutations in gene converting animals. Such humanized Ig or antibodies are not "human" since they are not naturally made by humans (since humans do not diversify their antibody repertoire through gene conversion) and yet, the humanized Ig or antibodies are not immunogenic to humans since they have human Ig sequences in their structure.

"Transgenes or transgene constructs" are DNA fragments with sequences encoding naturally or synthetic proteins normally not found in the animal or cells of the animal. The term "transgene construct" is used herein to refer to a polynucleotide molecule, which contains a structural "gene of interest" and other sequences facilitating gene transfer. This invention refers to at least two transgene constructs: 1) the rabbit bcl-2 apoptosis inhibitor transgene driven by a B-cell specific promoter, and, 2) the human Ig locus-self-cleaving peptide-apoptosis-inhibitor transgene construct.

"A transgenic expression vector or expression construct" refers to DNA fragments which encode, besides one or several transgene constructs of the invention, other regulatory DNA sequences required either for temporal, cell specific, or enhanced expression of the transgene(s) of interest, within specific cells of the non-human transgenic animal.

The "human(ized) Ig locus—self-cleaving peptide—apoptosis-inhibitor transgene or transgene construct" refers to a transgene construct that is transcribed into a single mRNA, which is translated into two polypeptides, namely, the human (ized) immunoglobulin chain and an apoptosis-inhibitor, due to a self-cleaving mechanism discussed below.

The term "self-cleaving peptide" as used herein refers to a peptide sequence that is associated with a cleavage activity that occurs between two amino acid residues within the peptide sequence itself. For example, in the 2A/2B peptide or in the 2A/2B-like peptides, cleavage occurs between the glycine residue on the 2A peptide and a proline residue on the 2B peptide. This occurs through a 'ribosomal skip mechanism' during translation wherein, normal peptide bond formation between the 2A glycine residue and the 2B proline residue of the 2A/2B peptide is impaired, without affecting the translation of the rest of the 2B peptide. Such ribosomal skip mechanisms are well known in the art and are known to be used by several viruses for the expression of several proteins encoded by a single messenger RNA.

The terms "endogenous Ig (immunoglobulin)-expressing B-cells" and "endogenous B-cells" are used interchangeably, and refer to those B-cells that express the animal's endogenous immunoglobulin locus.

The terms "exogenous Ig (immunoglobulin)-expressing B-cells" and "exogenous B cells" refer to those B-cells of a non-human animal that undergo productive rearrangement of an exogenous human(ized) Ig translocus introduced into such B-cells. The human(ized) Ig locus is introduced into such B-cells as a separate expression construct or as part of the same expression construct also encoding the apoptosis-inhibitor. Productive rearrangement of the human(ized) Ig locus results in the expression of the human(ized) Ig. and the transgene encoded apoptosis-inhibitor. As a result, apoptosis in B-cells expressing exogenous immunoglobulin is inhibited and cell survival is enhanced.

By "B-cell specific expression of the apoptosis inhibitor gene" is meant, expression of the apoptosis inhibitor gene product preferably within immune cells, more preferably within B-cells. Specific expression of the apoptosis inhibitor gene within immune cells or B-cells is achieved using immune-specific or preferably, using B-cell specific promoters to drive the expression of the apoptosis inhibitor gene.

By "selective expression of the apoptosis-inhibitor" is meant, expression of the apoptosis-inhibitor gene product preferentially within exogenous B-cells rather than within endogenous B cells expressing the native immunoglobulins of the transgenic animal. Preferably, the expression level of the apoptosis-inhibitor is at least about 2-fold, more preferably at least about 5-fold, even more preferably at least about 10-fold, most preferably at least about 50-fold more in exogenous B-cells as compared to expression in endogenous B-cells.

"Antibodies" (Abs) and "immunoglobulins" (Igs) are glycoproteins having the same structural characteristics. While antibodies exhibit binding specificity to a specific antigen, immunoglobulins include both antibodies and other antibody-like molecules which lack antigen specificity. The term "antibody" is used herein in the broadest sense and specifically covers, without limitation, monoclonal antibodies (including full length monoclonal antibodies), polyclonal antibodies, multispecific antibodies (e.g., bispecific antibodies), and antibody fragments so long as they exhibit the desired specificity.

The term "Ig gene segment" as used herein refers to segments of DNA encoding various portions of an Ig molecule, which are present in the germline of animals and humans, and which are brought together in B-cells to form rearranged Ig genes. Thus, Ig gene segments as used herein include V gene segments, D gene segments, J gene segments and C region gene segments. Functional rearrangement of VDJ or VJ segments results in the expression of immunoglobulin heavy or light chain.

The terms "antibody diversity" and "antibody repertoire" are used interchangeably, and refer to the total of all antibody specificities that an organism is capable of expressing.

An Ig locus having the capacity to undergo gene rearrangement and gene conversion is also referred to herein as a "functional" Ig locus, and the antibodies with a diversity generated by a functional Ig locus are also referred to herein as "functional" antibodies or a "functional" repertoire of antibodies.

The term "monoclonal antibody" is used to refer to an antibody molecule synthesized by a single clone of B-cells.

The term "polyclonal antibody" is used to refer to a population of antibody molecules synthesized by a population of B-cells.

The terms "polynucleotide" and "nucleic acid" are used interchangeably, and, when used in singular or plural, generally refer to any polyribonucleotide or polydeoxyribonucleotide, which may be unmodified RNA or DNA or modified RNA or DNA. Thus, for instance, polynucleotides as defined herein include, without limitation, single- and double-stranded DNA, DNA including single- and double-stranded regions, single- and double-stranded RNA, and RNA including single- and double-stranded regions, hybrid molecules comprising DNA and RNA that may be single-stranded or, more typically, double-stranded or include single- and double-stranded regions. In addition, the term "polynucleotide" as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. The term "polynucleotide" specifically includes cDNAs. The term includes DNAs (including cDNAs) and RNAs that contain one or more modified bases. Thus, DNAs or RNAs with backbones modified for stability or for other reasons are "polynucleotides" as that term is intended herein. Moreover, DNAs or RNAs comprising unusual bases, such as inosine, or modified bases, such as tritiated bases, are included within the term "polynucleotides" as defined herein. In general, the term "polynucleotide" embraces all chemically, enzymatically and/or metabolically modified forms of unmodified polynucleotides, as well as the chemical forms of DNA and RNA characteristic of viruses and cells, including simple and complex cells.

The term "non-human (transgenic) animal" as used herein includes, but is not limited to, mammals such as, for example, non-human primates, rodents (e.g. mice and rats), non-rodent mammals, such as, for example, rabbits, pigs, sheep, goats, cows, pigs, horses and donkeys, and birds (e.g., chickens, turkeys, ducks, geese and the like). The term "non-primate animal" as used herein includes, but is not limited to, mammals other than primates, including but not limited to the mammals specifically listed above.

The phrase "animals which create antibody diversity substantially by gene conversion and/or somatic hypermutation to create primary antibody repertoires" or "gene converting animals" and their grammatical equivalents, are used to refer to such animals in which the predominant mechanism of antibody diversification is gene conversion and/or hypermutation as opposed to gene rearrangement. Such animals include, but are not limited to, rabbits, birds (e.g., chickens, turkeys, ducks, geese and the like), cows and pigs. Particularly preferred non-human animals are rabbits and chickens.

By animals "stopping antibody gene rearrangement early in life" is meant those animals where the rearrangement of immunoglobulin genes stops typically within the first month of life. Examples of such animals are, without limitation, rabbits, birds (e.g. chickens), sheep, goats, cattle, swine and horses.

DETAILED DESCRIPTION

This invention, at least in part, is based on the recognition that the production of immunoglobulin (including immunoglobulin chains) in a non-human transgenic animal undergoing short-term lymphopoiesis can be significantly increased by expressing an apoptosis inhibitor in the B cells of the animal. As a result, the survival of B cells is enhanced and the production of immunoglobulin is increased.

The invention is further based on the identification on a novel apoptosis inhibitor, rabbit bcl-2. Accordingly, in one embodiment, the invention relates to methods for increasing immunoglobulin expression in non-human transgenic animals by overexpressing rabbit bcl-2 in the animals' B cells, using a B-cell specific promoter, thereby enhancing B-cell survival.

This invention further relates to a method for selectively enhancing the survival of exogenous B-cells, that is, B-cells expressing an immunoglobulin transgene locus, over the survival of endogenous B-cells that do not express such a transgene locus in non-human animals, undergoing short-term lymphopoiesis. Selectivity is achieved by coupling exogenous immunoglobulin expression with apoptosis inhibitor expression. In endogenous B-cells, the apoptosis inhibitor is not expressed and hence, apoptosis is not inhibited. Such selective expression results in the preferential production of the transgene expressed immunoglobulin over the endogenously produced immunoglobulin of the transgenic animal.

Overexpression of bcl-2 apoptosis inhibitors (other than the rabbit sequence first disclosed herein) has mainly been studied in mice which showed amplified and prolonged antibody responses to immunization due to a great excess of B lymphocytes, immunoglobulin-secreting cells, and serum immunoglobulins, attributable to increased longevity of B-lineage cells and antigen-specific memory B cells; McDonnell et al., *Cell*, 57:79-88, (1989); Strasser et al., *Current Topics in Microbiology and Immunology*, 166:175-181, (1990); Knott et al., *Hybridoma*, 15 (5):365-371, (1996); Smith et al., *J. Exp. Med.*, 191(3):475-784 (2000); Strasser et al., *PNAS*, 88:8661-8665, (1991) and Kumar et al., *Immunology Letters*, 65:153-159, (1999).

Apoptosis of targeted B-cell populations occurs routinely throughout B-cell development. Two major strategies for B-cell development have been identified through the study of different species: continuous B lymphopoiesis, as found in mice and humans, and short-term B lymphopoiesis followed by expansion in gut-associated lymphoid tissue (GALT), as found in chickens, rabbits, sheep and cows (reviewed in Lanning D, Osborne B A, Knight, K L., Immunoglobulin genes and generation of antibody repertoires in higher vertebrates: a key role of GALT. Molecular Biology of B-cells. Alt F. W., Honjo T, Nueberger, M. S., Eds. Elsevier London, p 443 (2004); and Flajnik M. F., Comparative analysis of immunoglobulin genes: surprises and portents. *Nat. Rev. Immunol.* 2:688, (2002)).

In species where continued B lymphopoiesis occurs, B-cells develop primarily in the bone marrow and fetal liver, and immunoglobulin genes diversify on-site through the process of combinatorial V(D)J joining. Most of the peripheral blood lymphocytes in such species are IgM$^+$, IgD$^+$, or naïve B-cells with undiversified VDJ and VJ genes, even in adults. Thus, there may be lesser pressure to produce a B-cell compartment quickly in animals with continued B lymphopoiesis since new B-cells with novel antigenic specificities are produced continuously.

In contrast, in the GALT (gut-associated lymphoid tissue) species where B lymphopoiesis is brief, an initial pool of B-cells is formed early in life in tissues such as the yolk sac and spleen, and thereafter, immunoglobulin (Ig) genes diversify in the GALT. Because B lymphopoiesis arrest is rapid, this initial B-cell compartment must expand and diversify quickly to generate antibodies with biologically relevant specificities. For instance, somatic diversification of Ig genes begins even before birth in chickens, sheep and cows. As a consequence, nearly all of the VDJ genes within the peripheral blood lymphocytes of adult rabbits for example, are highly diversified and lack naïve B-cells. Yet, the adult rabbit is very capable of mounting primary antibody responses to previously unseen antigens. That is because B-cells migrating from the GALT to the periphery appear to be of the primary B-cell repertoire, and even though their VDJ genes are already diversified, these long-lived and/or self-renewing B-cells can maintain the functional antibody repertoire. It is also likely that, as in the case of rabbits, exogenous antigenic stimulation helps drive the diversification of the antibody repertoire in species with short B lymphopoiesis.

In normal mice, during primary T cell-dependent immune responses, somatic mutations of Ig V region genes occurs in germinal-center-B-cells thus generating variant B-cells that express immunoglobulins with altered affinities for the antigen. Variants with improved affinity are positively selected through the inhibition of apoptosis and eventually, such high affinity B-cells make up the majority of the antigen specific memory and antibody-forming B-cell populations. B-cells with a low affinity receptor fail to receive such antigen-dependent survival signals and undergo apoptosis. Such an increase in high-affinity B-cells, within memory and antibody-forming B-cell populations, is referred to as affinity maturation.

In bcl-2 transgenic mice, overexpression of bcl-2 results in the prevention of apoptosis not only of high affinity B-cells, but also of low affinity B-cells. Bcl-2 overexpressing mice have an excessive number of memory B-cells that are not affinity selected. In contrast, the stringent selection of high-affinity bone marrow antibody-forming cells in the bcl-2 mouse is not influenced by the bcl-2 transgene and their numbers remain unchanged compared to controls.

While the effects of overexpression of bcl-2 on B-cell survival and development in other animals undergoing continuous B lymphopoiesis may be similar to that in mice, its role in the development of memory and/or antibody-forming B-cells of animals undergoing short-term B lymphopoiesis is unclear.

Therefore, the present invention is directed to methods for overexpressing apoptosis inhibitors, particularly in animals with short-term B lymphopoiesis like rabbits, birds, chickens, sheep, goats, cows, swine, horses and donkeys and enhancing B-cell survival in such transgenic animals. In addition, when these animals further express an Ig translocus, expression of the Ig translocus is enhanced or prolonged and since these are larger animals, their antibody yields should also be greater. Thus, this invention aims at creating larger founder animals producing higher amounts exogenous immunoglobulins through enhanced B-cell survival.

In one aspect, the present invention is directed to transgenic constructs useful for enhancing the survival of B-cells. Transgenes or transgene constructs are DNA fragments with sequences encoding for one, or several, natural or synthetic proteins not normally found in the animal or cells of the animal. The DNA fragment(s) may be introduced into the animal's genome by a variety of techniques including microinjection of pronuclei, transfection, nuclear transfer cloning, sperm-mediated gene transfer, testis-mediated gene transfer, and the like.

In one embodiment, the transgene construct comprises the nucleic acid molecule encoding the apoptosis inhibitor, rabbit bcl-2 polypeptide. By "nucleic acid molecule encoding the apoptosis inhibitor" is meant the native DNA sequence, as well as any codon optimized DNA sequence which encodes for the a polypeptide sequence identical to the native DNA sequence, but which has a different DNA sequence based on codon degeneracy. This concept is discussed in detail below. In another embodiment, the transgene construct comprises the nucleic acid molecule encoding any apoptosis inhibitor. The apoptosis-inhibitor gene, such as the rabbit bcl-2 gene or the human bcl-2 gene, is preferably expressed in B-cells of the transgenic animal by means of an immune-specific promoter, preferably a B-cell specific promoter. Therefore, apoptosis-inhibitor expression is enhanced preferably within B-cells alone leading to enhanced B-cell survival in the non-human transgenic animal. By "B-cell specific promoter" is meant the promoter/enhancers sequence of any B-cell specific genes, and/or variants or engineered portions thereof, that normally controls the expression of genes expressed in a B-cell, examples of which include, but are not limited to, promoters/enhancers of CD19, CD20, CD21, CD22, CD23, CD24, CD40, CD72, Blimp-1, CD79b (also known as B29 or Ig beta), mb-1 (also known as Ig alpha), tyrosine kinase blk, VpreB, immunoglobulin heavy chain, immunoglobulin kappa light chain, immunoglobulin lambda-light chain, immunoglobulin J-chain, etc. In a preferred embodiment, the kappa light chain promoter/enhancer drives the B-cell specific expression of the rabbit bcl-2 apoptosis-inhibitor gene.

In yet another embodiment, the transgene construct comprising the nucleic acid molecule encoding the apoptosis inhibitor is coexpressed with a transgene construct comprising an exogenous immunoglobulin or immunoglobulin (Ig) chain transgene locus. In this embodiment, both the Ig transgene locus and the apoptosis inhibitor transgene may be present on the same transgenic expression vector or on two different transgenic expression vectors. In the latter case, the two transgenic expression vectors may be introduced into the non-human transgenic animal either at the same time or sequentially.

The present invention also provides transgene constructs comprising a chimeric transgene that encodes for a fusion protein comprising a transgene encoding a fusion-protein comprising polypeptide sequences in the following order: a) an immunoglobulin or immunoglobulin chain; b) a self-cleaving peptide; c) an apoptosis inhibitor; and optionally, d) a protease cleavage site between a) and b). Here, the expression of the apoptosis inhibitor is linked or coupled to the expression of the immunoglobulin heavy or light chain using mechanisms discussed below. This transgenic construct is also referred to as the Ig locus-protease cleavage site-self cleaving peptide-apoptosis inhibitor construct. In this construct, a protease cleavage site is optionally added to facilitate the removal of the F2A self-cleaving peptide sequence from the immunoglobulin; for instance, from the M2-exon of the Ig, to prevent any potential interference of the F2A peptide sequence with signaling (and therefore B-cell development). The protease cleavage sites can be recognized by any constitutively expressed proteases. Protease cleavage sites useful herein include, but are not limited to, aspartic proteases, cysteine proteases, metalloproteases, serine proteases threonine proteases, etc. In a preferred embodiment, the protease cleavage site is the furin cleavage site.

The chimeric transgenes described above comprises DNA sequences encoding for a self cleaving peptide (for example, 2A peptide or 2A-like peptide). Insertion of a self-cleaving peptide-encoding sequence between the immunoglobulin-encoding sequence and an apoptosis-inhibitor sequence in the transgene results in production of one messenger RNA. Translation of this mRNA, however, results in two separate proteins, the immunoglobulin(s) and the apoptosis-inhibitor, due to the peptide's self-cleaving mechanism. Therefore, expression of the apoptosis-inhibitor can be coupled to the functional rearrangement of VDJ or VJ segments.

In one such embodiment of the invention, the self-cleaving is mediated by 2A/2B peptides, or 2A-like/2B sequences of viruses that include the picornaviridae virus family, the equine rhinitis A (ERAV) virus family, the picornavirus-like insect virus family or from the type C rotavirus family. The picornaviridae virus family includes the entero-, rhino-, cardio- and aphtho- and foot-and-mouth disease (FMDV) viruses. The picornavirus-like insect virus family includes viruses such as the infectious flacherie virus (IFV), the Drosophila C virus (DCV), the acute bee paralysis virus (ABPV) and the cricket paralysis virus (CrPV) and the insect virus Thosea asigna virus (TaV). The type C rotavirus family includes the bovine, porcine and human type C rotaviruses. In further embodiments, the cleavage sequences may include 2A-like/2B sequences from either the poliovirus, rhinovirus, coxsackie virus, encephalomyocarditis virus (EMCV), mengovirus, the porcine teschovirus-1, or the Theiler's murine encephalitis virus (TMEV), etc. In a preferred embodiment, the self-cleaving protein sequence is either the 2A/2B peptide of the foot and mouth disease virus (FMDV), the equine rhinitis A (ERAV) virus, or the Thosea asigna virus (TaV); Palmenberg et al., Virology 190:754-762 (1992); Ryan et al., J Gen Virol 72:2727-2732 (1991); Donnelly et al., J Gen Virol 82:1027-1041 (2001); Donnelly et al., J Gen Virol 82:1013-1025 (2001); Szymaczak et al., Nature Biotech 22(5):589-594 (2004). Thus, using the self-cleaving peptide, expression of the apoptosis inhibitor gene is linked or coupled to the expression of the Ig translocus within exogenous B-cells. Selective survival of exogenous B-cells over endogenous B-cells results in reduced endogenous immunoglobulin production but in a corresponding increase in production of the Ig translocus encoded polypeptide/protein.

While bcl-2 is discussed as a prototype of apoptosis-inhibitors, other apoptosis-inhibitors are also included for use in the chimeric transgene construct. These include, without limitation, caspase-9 dominant negative (caspase-9-DN) mutants, baculovirus p35, caspase-9S, crmA, z-VAD-fmk, z-DEVD-fmk, B-D-fmk, and z-YVAD-fmk, other bcl-2 family members like Bcl-$x_L$, Mcl-1, etc., inhibitors of proapoptotic molecules like Bax, Bak, Bad, inhibitors of "BH3 domain only" molecules like Bid, Bim, PUMA, Noxa, etc., other endogenous caspase inhibitors like IAP (inhibitor of apoptosis proteins) including, but not limited to XIAP, TIAP, KIAP, NAIP, cIAP1, cIAP2, API1, API2, API3, API4, HIAP1, HIAP2, MIHA, MIHB, MIHC, ILP, ILP-2, TLAP, survivin, livin, apollon, BRUCE, and MLIAP, etc., proteins like SODD and FLIP, etc. involved in the down-regulation of death receptors and variants thereof. In a specific embodiment, the apoptosis inhibitor gene may be a mammalian bcl-2 gene and in preferred embodiments, the mammalian bcl-2 gene is selected from the group consisting of human bcl-2, mouse bcl-2 and rabbit bcl-2 of SEQ ID NO: 5. In a preferred embodiment, the rabbit bcl-2 gene of SEQ ID NO: 5 is used.

In yet another aspect of the invention, the transgene encodes immunoglobulin heavy chains and/or immunoglobulin light chains or parts thereof. The loci can be in germline configuration or in a rearranged form. The coding sequences or parts thereof may code for human immunoglobulins resulting in the expression of human(ized) antibodies.

The transgene(s) encoding human(ized) antibodies contain(s) an Ig locus or a large portion of an Ig locus, containing one or several human Ig segments (e.g., a human Ig V, D, J or C gene segment). Alternatively, the transgene is a human immunoglobulin locus or a large portion thereof. The transgene containing such a human Ig locus or such modified Ig locus or modified portion of an Ig locus, also referred to herein as "a human(ized) Ig translocus", is capable of undergoing gene rearrangement in the transgenic non-human animal thereby producing a diversified repertoire of antibodies having at least a portion of a human immunoglobulin polypeptide sequence.

Immunoglobulin heavy and light chain genes comprise several segments encoded by individual genes and separated by intron sequences. Thus genes for the human immunoglobulin heavy chain are found on chromosome 14. The variable region of the heavy chain (VH) comprises three gene segments: V, D and J segments, followed by multiple genes coding for the C region. The V region is separated from the C region by a large spacer, and the individual genes encoding the V, D and J segments are also separated by spacers.

There are two types of immunoglobulin light chains: κ and λ. Genes for the human κ light chain are found on chromosome 2 and genes for the human λ light chain are found on chromosome 22. The variable region of antibody light chains includes a V segment and a J segment, encoded by separate gene segments. In the germline configuration of the κ light chain gene, there are approximately 100-200 V region genes in linear arrangement, each gene having its own leader sequence, followed by approximately 5 J gene segments, and C region gene segment. All V regions are separated by introns, and there are introns separating the V, J and C region gene segments as well.

Additionally, the vectors containing either of the transgene constructs described above may further contain DNA sequences coding for antibiotic selection markers like gentamycin, neomycin or kanamycin etc. and/or other conventional components of expression vectors.

The present invention provides methods for enhancing the expression of immunoglobulins in a non-human transgenic animal undergoing short-term lymphopoiesis comprising introducing into the transgenic animal undergoing short-term lymphopoiesis, at least one transgene construct comprising an apoptosis-inhibitor transgene driven by a B-cell specific promoter/enhancer. Thus, apoptosis of such B-cells with the transgene construct is inhibited and production of the immunoglobulin or immunoglobulin chain is enhanced. In a further embodiment of this method, the non-human transgenic animal undergoing short-term lymphopoiesis may further comprise an exogenous immunoglobulin(s) or immunoglobulin chain transgene locus. This results in higher yields of the exogenous immunoglobulin which can greatly simplify antibody purification and production. In this instance, the apoptosis-inhibitor gene may be introduced, either, as part of a transgenic expression construct that also introduces the Ig translocus, or on different transgenic constructs.

The invention further provides another method for selectively enhancing the expression of an exogenous immunoglobulin(s)/immunoglobulin chain within an exogenous B-cell of a non-human transgenic animal, where expression of the exogenous immunoglobulin(s)/immunoglobulin chain and an apoptosis inhibitor transgene within the exogenous B-cell is coupled. Correspondingly, there is no expression of the apoptosis inhibitor in endogenous B-cells, or B-cells not expressing the Ig translocus. Due to productive rearrangement of the exogenous immunoglobulin translocus and an increase in exogenous B-cell survival, transgene-encoded immunoglobulin production is increased over endogenous immunoglobulin production. Thus, survival of the exogenous B cell is enhanced and exogenous immunoglobulin(s)/immunoglobulin chain production is also enhanced.

The present invention further provides nucleic acid sequences that encode for proteins, polypeptides or peptide sequences for rabbit bcl-2, which is an apoptosis-inhibitor. It is also contemplated that a given nucleic acid sequence for rabbit bcl-2 may be represented by natural variants that have slightly different nucleic acid sequences but, nonetheless, encode the same protein. Furthermore, the term functionally equivalent codon is used herein to refer to codons that encode the same amino acid, for example, as the six codons for arginine or serine, and also refers to codons that encode biologically equivalent amino acids, as discussed herein.

The rabbit bcl-2 DNA segments used in the present invention encompass biologically functional equivalent modified polypeptides and peptides. Such sequences may arise as a consequence of codon redundancy and functional equivalency that are known to occur naturally within nucleic acid sequences and the proteins thus encoded. Alternatively, functionally equivalent proteins or peptides may be created via the application of recombinant DNA technology, in which changes in the protein structure may be engineered, based on considerations of the properties of the amino acids being exchanged. Changes designed by human may be introduced through the application of site-directed mutagenesis techniques, e.g., to introduce improvements to the antigenicity of the protein, to reduce toxicity effects of the protein in vivo to a subject given the protein, or to increase the efficacy of any treatment involving the protein.

Allowing for the degeneracy of the genetic code, the invention encompasses sequences that have at least about 50%, usually at least about 60%, more usually about 70%, most usually about 80%, preferably at least about 90% and most preferably about 95% sequence identity to the nucleotide sequence of the rabbit bcl-2 gene or the human bcl-2 gene, respectively. These are also referred to as codon optimized sequences and is discussed below under functionally equivalent codons.

The term biologically functional equivalent is well understood in the art and is further defined in detail herein. Accordingly, sequences that have between about 70% and about 80%; or more preferably, between about 81% and about 90%; or even more preferably, between about 91% and about 99% identical at the amino acid level are considered functionally equivalent to the rabbit bcl-2 polypeptide, provided the biological activity of the protein is maintained.

The term functionally equivalent codon is used herein to refer to codons that encode the same amino acid, such as the six codons for arginine or serine, and also refers to codons that encode biologically equivalent amino acids.

The following is a discussion based upon changing of the amino acids of a protein to create an equivalent, or even an improved, second-generation molecule. For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid substitutions can be made in a protein sequence, and in its underlying DNA coding sequence, and nevertheless produce a protein with like properties. It is thus contemplated by the inventors that various changes may be made in the DNA sequences of genes without appreciable loss of their biological utility or activity, as discussed below.

In making such changes, the hydropathic index of amino acids may also be considered. The importance of the hydropathic amino acid index in conferring interactive biologic function on a protein is generally understood in the art (Kyte & Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

It also is understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: arginine (+3.0); lysine (+3.0); aspartate (+3.0.+−0.1); glutamate (+3.0.+−0.1); serine (+0.3); asparagine (+0.2) glutamine (+0.2); glycine (0); threonine (−0.4); proline (−0.5.+−0.1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

It is understood that an amino acid can be substituted for another having a similar hydrophilicity value and still produce a biologically equivalent and immunologically equivalent protein. In such changes, the substitution of amino acids whose hydrophilicity values are within .+−0.2 is preferred, those that are within .+−0.1 are particularly preferred, and those within .+−.0.5 are even more particularly preferred.

As outlined herein, amino acid substitutions generally are based on the relative similarity of the amino acid side-chain substituents, for example, their hydrophobicity, hydrophilicity, charge, size, and the like. Exemplary substitutions that take into consideration the various foregoing characteristics are well known to those of skill in the art and include: arginine and lysine; glutamate and aspartate; serine and threonine; glutamine and asparagine; and valine, leucine and isoleucine.

Another embodiment for the preparation of polypeptides according to the invention is the use of peptide mimetics. Mimetics are peptide-containing molecules that mimic elements of protein secondary structure (Johnson 1993). The underlying rationale behind the use of peptide mimetics is that the peptide backbone of proteins exists chiefly to orient amino acid side chains in such a way as to facilitate molecular interactions, such as those of antibody and antigen. A peptide mimetic is expected to permit molecular interactions similar to the natural molecule. These principles may be used, in conjunction with the principles outlined above, to engineer second generation molecules having many of the natural properties of apoptosis-inhibitors with altered and improved characteristics.

Thus, variant nucleic acid sequences that encode for rabbit bcl-2 and functionally equivalent polypeptides of rabbit bcl-2 are useful as apoptosis-inhibitors in this invention.

The immune system's capacity to protect against infection rests in a genetic machinery specialized to create a diverse repertoire of antibodies. Antibody-coding genes in B-cells are assembled in a manner that allows to countless combinations of binding sites in the variable (V) region. It is estimated that more than $10^{12}$ possible binding structures arise from such mechanisms. In all animals, including humans, the antibody-making process begins by recombining variable (V), diversity (D) and joining (J) segments of the immunoglobulin (Ig) locus. Following this step, depending on the animal species, two general mechanisms are used to produce the diverse binding structures of antibodies.

In some animals, such as human and mouse, there are multiple copies of V, D and J gene segments on the immunoglobulin heavy chain locus, and multiple copies of V and J gene segments on the immunoglobulin light chain locus. Antibody diversity in these animals is generated primarily by gene rearrangement, i.e., different combinations of gene segments to form rearranged heavy chain variable region and light chain variable region. In other animals (e.g., rabbit, birds, e.g., chicken, goose, and duck, sheep, goat, and cow), however, gene rearrangement plays a smaller role in the generation of antibody diversity. For example, in rabbit, only a very limited number of the V gene segments, most often the V gene segments at the 3' end of the V-region, is used in gene rearrangement to form a contiguous VDJ segment. In chicken, only one V gene segment (the one adjacent to the D region, or "the 3' proximal V gene segment"), one D segment and one J segment are used in the heavy chain rearrangement; and only one V gene segment (the 3' proximal V segment) and one J segment are used in the light chain rearrangement. Thus, in these animals, there is little diversity among initially rearranged variable region sequences resulting from junctional diversification. Further diversification of the rearranged Ig genes is achieved by gene conversion a process in which short sequences derived from the upstream V gene segments replace short sequences within the V gene segment in the rearranged Ig gene. Additional diversification of antibody sequences may be generated by hypermutation.

Immunoglobulins (antibodies) belong into five classes (IgG, IgM, IgA, IgE, and IgD, each with different biological roles in immune defense. The most abundant in the blood and potent in response to infection is the IgG class. Within the human IgG class, there are four sub-classes (IgG1, IgG2, IgG3 and IgG4 isotypes) determined by the structure of the heavy chain constant regions that comprise the Fc domain. The F(ab) domains of antibodies bind to specific sequences (epitopes) on antigens, while the Fc domain of antibodies recruits and activates other components of the immune system in order to eliminate the antigens.

Native antibodies and immunoglobulins are usually heterotetrameric glycoproteins of about 150,000 daltons, composed of two identical light (L) chains and two identical heavy (H) chains. Each light chain is linked to a heavy chain by covalent disulfide bond(s), while the number of disulfide linkages varies between the heavy chains of different immunoglobulin isotypes. Each heavy and light chain also has regularly spaced intrachain disulfide bridges. Each heavy chain has at one end a variable domain (VH) followed by a number of constant domains. Each light chain has a variable domain at one end (VL) and a constant domain at its other end; the constant domain of the light chain is aligned with the first constant domain of the heavy chain, and the light chain variable domain is aligned with the variable domain of the heavy chain. Particular amino acid residues are believed to form an interface between the light- and heavy-chain variable domains (Chothia et al., *J. Mol. Biol.* 186:651 (1985); Novotny and Haber, *Proc. Natl. Acad. Sci. U.S.A.* 82:4592 (1985)).

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called complementarity-determining regions (CDRs) or hypervariable regions both in the light-chain and the heavy-chain variable domains. The more highly conserved portions of variable domains are called the framework (FR). The variable domains of native heavy and light chains each comprise four FR regions, connected by three CDRs. The CDRs in each chain are held together in close proximity by the FR regions and, with the CDRs from the other chain, contribute to the formation of the antigen-binding site of antibodies (see Kabat et al., *Sequences of Proteins of Immunological Interest*, Fifth Edition, National Institute of Health, Bethesda, Md. (1991)). The constant domains are not involved directly in binding an antibody to an antigen, but exhibit various effector functions, such as participation of the antibody in antibody-dependent cellular toxicity.

The creation of human-animal translocus allows for the creation of transgenic animals that express diversified, high-affinity human(ized) (polyclonal) antibodies in high yields. In general, the humanization of an immunoglobulin (Ig) locus in a non-human animal involves the integration of one or more human Ig gene segments into the animal's genome to create human(ized) immunoglobulin loci. Thus, creation of a human (ized) Ig heavy chain locus involves the integration of one or more V and/or D and/or J segments, and/or C region segments into the animal's genome. Similarly, the creation of a humanized Ig light chain locus involves the integration of one or more V and/or J segments, and/or C region segments into the animal's genome.

Regardless of the chromosomal location, the human(ized) Ig locus of the present invention has the capacity to undergo gene rearrangement and gene conversion and hypermutation in the non-human animal, thereby producing a diversified repertoire of human(ized) Ig molecules. An Ig locus having the capacity to undergo gene rearrangement and gene conversion is also referred to as a "functional" Ig locus and the antibodies with a diversity generated by a functional Ig locus are also referred to as "functional" antibodies or a "functional" repertoire of antibody molecules.

In one aspect, animals in which diversification of the antibody repertoire stops early in life are useful in the current invention. B-cells develop from hematopoietic stem cells. Prior to antigen exposure, B-cells undergo a series of maturation steps the end product of which is a mature B-cell, which expresses a unique membrane-associated IgM and often IgD on its cell surface along with other cell surface signaling molecules. While in humans, antibody diversification by gene rearrangement occurs throughout life, in other animals the diversification of antibody repertoire stops early in life, typically within the first month of life.

In one aspect of this invention, the animals to whom the DNA constructs of the invention can be administered include, but are not limited to, mammals (e.g. humans, non-human primates, rodents (e.g. mice and rats), non-rodents (e.g. rabbits, pigs, sheep, goats, cows, pigs, horses and donkeys), and birds (e.g., chickens, turkeys, ducks, geese and the like). The animals to whom the DNA constructs of the invention can be administered include 'gene converting animals', that is, animals that create antibody diversity substantially by gene conversion and/or somatic hypermutation (for e.g. rabbits, birds, cows, swine, etc.), and animals where antibody rearrangement stops early in life, that is, typically, within the first month of life (for e.g. rabbits, birds, sheep, goats, cattle, swine, horses, etc.).

Further, animals to whom the DNA constructs of the invention can be administered also include any of the non-human animal described above, further carrying a transgene encoding an exogenous immunoglobulin translocus, preferably, a human or humanized immunoglobulin heavy chain and/or immunoglobulin light chain sequence or parts thereof. The transgene locus can be either in the germline configuration or in a rearranged form. Since the transgenes encode for human or humanized immunoglobulins or parts thereof, it results in the generation of humanized antibodies. Thus, for example, using the methods described above, enhanced production of humanized antibodies, can be generated in target non-human animals using the rabbit bcl-2 apoptosis-inhibitor described in this invention.

According to the present invention, a transgenic animal capable of making human(ized) immunoglobulins is made by introducing into a recipient cell or cells of an animal, one or more of the transgenic vectors described herein above, one of which carries a human(ized) Ig locus, and deriving an animal from the genetically modified recipient cell or cells.

The recipient cells may, for example, be from non-human animals which generate antibody diversity by gene conversion and/or hypermutation, e.g., bird (such as chicken), rabbit, cows and the like. In such animals, the 3'proximal V gene segment is preferentially used for the production of immunoglobulins. Integration of a human V gene segment into the Ig locus on the transgene vector, either by replacing the 3' proximal V gene segment of the animal or by being placed in close proximity of the 3' proximal V gene segment, results in expression of human V region polypeptide sequences in the majority of immunoglobulins. Alternatively, a rearranged human V(D)J segment may be inserted into the J locus of the immunoglobulin locus on the transgene vector.

The transgenic vectors containing the genes of interest, namely, the human(ized) Ig locus and the apoptosis-inhibitor gene may be introduced into the recipient cell or cells and then integrated into the genome of the recipient cell or cells by random integration or by targeted integration.

For random integration, a transgenic vector containing a human(ized) Ig locus can be introduced into an animal recipient cell by standard transgenic technology. For example, a transgenic vector can be directly injected into the pronucleus of a fertilized oocyte. A transgenic vector can also be introduced by co-incubation of sperm with the transgenic vector before fertilization of the oocyte. Transgenic animals can be developed from fertilized oocytes. Another way to introduce a transgenic vector is by transfecting embryonic stem cells and subsequently injecting the genetically modified embryonic stem cells into developing embryos. Alternatively, a transgenic vector (naked or in combination with facilitating reagents) can be directly injected into a developing embryo. Ultimately, chimeric transgenic animals are produced from the embryos which contain the human(ized) Ig transgene integrated in the genome of at least some somatic cells of the transgenic animal.

In a particular embodiment, a transgene containing a human(ized) Ig locus is randomly integrated into the genome of recipient cells (such as fertilized oocyte or developing embryos) derived from animal strains with an impaired expression of endogenous immunoglobulin genes. The use of such animal strains permits preferential expression of immunoglobulin molecules from the human(ized) transgenic Ig locus. Examples for such animals include the Alicia and Basilea rabbit strains, as well as agammaglobinemic chicken strain, as well as immunoglobulin knock-out mice. Alternatively, transgenic animals with human(ized) immunoglobulin transgenes or loci can be mated with animal strains with impaired expression of endogenous immunoglobulins. Offspring homozygous for an impaired endogenous Ig locus and a human(ized) transgenic Ig locus can be obtained.

For targeted integration, a transgenic vector can be introduced into appropriate animal recipient cells such as embryonic stem cells or already differentiated somatic cells. Afterwards, cells in which the transgene has integrated into the animal genome and has replaced the corresponding endogenous Ig locus by homologous recombination can be selected by standard methods See for example, Kuroiwa et al, Nature Genetics 2004, June 6. The selected cells may then be fused with enucleated nuclear transfer unit cells, e.g. oocytes or embryonic stem cells, cells which are totipotent and capable of forming a functional neonate. Fusion is performed in accordance with conventional techniques which are well established. Enucleation of oocytes and nuclear transfer can also be performed by microsurgery using injection pipettes. (See, for example, Wakayama et al., Nature (1998) 394:369.) The resulting egg cells are then cultivated in an appropriate medium, and transferred into synchronized recipients for generating transgenic animals. Alternatively, the selected genetically modified cells can be injected into developing embryos which are subsequently developed into chimeric animals.

Further, according to the present invention, a transgenic animal capable of producing human(ized) immunoglobulins can also be made by introducing into a recipient cell or cells, one or more of the recombination vectors described herein above, one of which carries a human Ig gene segment, linked to 5' and 3' flanking sequences that are homologous to the flanking sequences of the endogenous Ig gene segment, then selecting cells in which the endogenous Ig gene segment is replaced by the human Ig gene segment by homologous recombination, and deriving an animal from the selected genetically modified recipient cell or cells.

Similar to the target insertion of a transgenic vector, cells appropriate for use as recipient cells in this approach include embryonic stem cells or already differentiated somatic cells. A recombination vector carrying a human Ig gene segment can be introduced into such recipient cells by any feasible means, e.g., transfection. Afterwards, cells in which the human Ig gene segment has replaced the corresponding endogenous Ig gene segment by homologous recombination, can be selected by standard methods. These genetically modified cells can serve as nuclei donor cells in a nuclear transfer procedure for cloning a transgenic animal. Alternatively, the selected genetically modified embryonic stem cells can be injected into developing embryos which can be subsequently developed into chimeric animals.

In a specific embodiment, the transgene constructs of the invention may be introduced into the transgenic animals during embryonic life by directly injecting the transgenes into the embryo or indirectly by injecting them into the pregnant mother or into the egg-laying hen. As a consequence, due to the inhibition of apoptosis in exogenous B-cells, transgenic offspring will have increased production of human(ized) antibodies in response to immunization with antigens.

Transgenic animals produced by any of the foregoing methods form another embodiment of the present invention. The transgenic animals have at least one, i.e., one or more, human(ized) Ig loci in the genome, from which a functional repertoire of human(ized) antibodies is produced.

In a specific embodiment, the present invention provides transgenic rabbits expressing one or more human(ized) Ig loci and an apoptosis-inhibitor gene. The transgenic rabbits of the present invention are capable of rearranging and gene converting the human(ized) Ig loci, and expressing a functional repertoire of human(ized) antibodies.

In another specific embodiment, the present invention provides transgenic chickens expressing one or more human (ized) Ig loci and a apoptosis-inhibitor gene. The transgenic chickens of the present invention are capable of rearranging and gene converting the human(ized) Ig loci, and expressing a functional repertoire of human(ized) antibodies. In another specific embodiment, the present invention provides transgenic mice expressing one or more human(ized) V regions and the rabbit bcl-2 apoptosis-inhibitor gene. The human (ized) V region comprises at least two human V gene segments flanked by non-human spacer sequences. The transgenic mice are capable of rearranging the human V elements and expressing a functional repertoire of antibodies.

Immunization with antigen leads to the production of human(ized) antibodies against the same antigen in said transgenic animals.

Although preferred embodiments of the present invention are directed to transgenic animals having human(ized) Ig loci, it is to be understood that transgenic animals having primatized Ig loci and primatized polyclonal antisera are also within the spirit of the present invention. Similar to human (ized) polyclonal antisera compositions, primatized polyclonal antisera compositions are likely to have a reduced immunogenicity in human individuals.

Once a transgenic non-human animal capable of producing diversified human(ized) immunoglobulin molecules is made (as further set forth below), human(ized) immunoglobulins and human(ized) antibody preparations against an antigen can be readily obtained by immunizing the animal with the antigen. A variety of antigens can be used to immunize a transgenic host animal. Such antigens include, microorganism, e.g. viruses and unicellular organisms (such as bacteria and fungi), alive, attenuated or dead, fragments of the microorganisms, or antigenic molecules isolated from the microorganisms.

Preferred bacterial antigens for use in immunizing an animal include purified antigens from *Staphylococcus aureus* such as capsular polysaccharides type 5 and 8, recombinant versions of virulence factors such as alpha-toxin, adhesin binding proteins, collagen binding proteins, and fibronectin binding proteins. Preferred bacterial antigens also include an attenuated version of *S. aureus, Pseudomonas aeruginosa, enterococcus, enterobacter*, and *Klebsiella pneumoniae*, or culture supernatant from these bacteria cells. Other bacterial antigens which can be used in immunization include purified lipopolysaccharide (LPS), capsular antigens, capsular polysaccharides and/or recombinant versions of the outer membrane proteins, fibronectin binding proteins, endotoxin, and exotoxin from *Pseudomonas aeruginosa, enterococcus, enterobacter*, and *Klebsiella pneumoniae*.

Preferred antigens for the generation of antibodies against fungi include attenuated version of fungi or outer membrane proteins thereof, which fungi include, but are not limited to, *Candida albicans, Candida parapsilosis, Candida tropicalis*, and *Cryptococcus neoformans*.

Preferred antigens for use in immunization in order to generate antibodies against viruses include the envelop proteins and attenuated versions of viruses which include, but are not limited to respiratory synctial virus (RSV) (particularly the F-Protein), Hepatitis C virus (HCV), Hepatits B virus (HBV), cytomegalovirus (CMV), EBV, and HSV.

Therapeutic antibodies can be generated for the treatment of cancer by immunizing transgenic animals with isolated tumor cells or tumor cell lines; tumor-associated antigens which include, but are not limited to, Her-2-neu antigen (antibodies against which are useful for the treatment of breast cancer); CD19, CD20, CD22 and CD53 antigens (antibodies against which are useful for the treatment of B-cell lymphomas), (3) prostate specific membrane antigen (PMSA) (antibodies against which are useful for the treatment of prostate cancer), and 17-1A molecule (antibodies against which are useful for the treatment of colon cancer).

The antigens can be administered to a transgenic host animal in any convenient manner, with or without an adjuvant, and can be administered in accordance with a predetermined schedule.

After immunization, serum or milk from the immunized transgenic animals can be fractionated for the purification of pharmaceutical grade polyclonal antibodies specific for the antigen. In the case of transgenic birds, antibodies can also be made by fractionating egg yolks. A concentrated, purified immunoglobulin fraction may be obtained by chromatography (affinity, ionic exchange, gel filtration, etc.), selective precipitation with salts such as ammonium sulfate, organic solvents such as ethanol, or polymers such as polyethyleneglycol.

The fractionated human(ized) antibodies may be dissolved or diluted in non-toxic, non-pyrogenic media suitable for intravenous administration in humans, for instance, sterile buffered saline.

The antibody preparations used for administration are generally characterized by having immunoglobulin concentrations from 0.1 to 100 mg/ml, more usually from 1 to 10 mg/ml. The antibody preparation may contain immunoglobulins of various isotypes. Alternatively, the antibody preparation may contain antibodies of only one isotype, or a number of selected isotypes.

For making a human(ized) monoclonal antibody, spleen cells are isolated from the immunized transgenic animal whose B-cells expressing the animal's endogenous immunoglobulin have been depleted. Isolated spleen cells are used either in cell fusion with transformed cell lines for the production of hybridomas, or cDNAs encoding antibodies are cloned by standard molecular biology techniques and expressed in transfected cells. The procedures for making monoclonal antibodies are well established in the art. See, e.g., European Patent Application 0 583 980 A1 ("Method For Generating Monoclonal Antibodies From Rabbits"), U.S. Pat. No. 4,977,081 ("Stable Rabbit-Mouse Hybridomas And Secretion Products Thereof"), WO 97/16537 ("Stable Chicken B-cell Line And Method of Use Thereof"), and EP 0 491 057 B1 ("Hybridoma Which Produces Avian Specific Immunoglobulin G"), the disclosures of which are incorporated herein by reference. In vitro production of monoclonal antibodies from cloned cDNA molecules has been described by Andris-Widhopf et al., "Methods for the generation of chicken monoclonal antibody fragments by phage display", *J Immunol Methods* 242:159 (2000), and by Burton, D. R., "Phage display", *Immunotechnology* 1:87 (1995), the disclosures of which are incorporated herein by reference.

In most instances the antibody preparation consists of unmodified immunoglobulins, i.e., human(ized) antibodies prepared from the animal without additional modification, e.g., by chemicals or enzymes. Alternatively, the immunoglobulin fraction may be subject to treatment such as enzymatic digestion (e.g. with pepsin, papain, plasmin, glycosidases, nucleases, etc.), heating, etc, and/or further fractionated.

Embodiments of the invention are directed to transgenes comprising the rabbit bcl-2 apoptosis-inhibitor which is expressed specifically in B-cells using a B-cell specific promoter. Another embodiment is directed to transgenes comprising the Ig locus-self-cleaving peptide-apoptosis inhibitor transgene, where expression of the apoptosis inhibitor gene is coupled to the expression of the Ig locus. Various apoptosis-inhibitor genes described above and those known in the art, including the rabbit bcl-2 apoptosis inhibitor, can be used in this embodiment.

Further embodiments of the invention are directed to methods to enhance the survival of B-cells using the transgene constructs described above. When the rabbit bcl-2 transgenic construct is used, the transgene can be introduced into a transgenic animal further comprising a transgene encoding an immunoglobulin locus thereby specifically enhancing the survival of B-cells. When the Ig locus-self-cleaving peptide-apoptosis inhibitor transgene is used, exogenous B-cells selectively survive and productively produce the transgene encoded gene. Selectivity is achieved by coupling exogenous immunoglobulin expression with apoptosis inhibitor expression. In endogenous B-cells, the apoptosis inhibitor is not expressed and hence, apoptosis is not inhibited. Such selective expression results in the preferential production of the desired transgene expressed immunoglobulin over the endogenously produced immunoglobulin of the transgenic animal. Any variety of apoptosis-inhibitors, self-cleaving peptides or immunoglobulin genes described herein or well-known in the art can be used in this transgene construct. In a preferred embodiment, the Ig locus of the transgene is a human(ized) immunoglobulin/immunoglobulin chain translocus.

The invention also provides a novel apoptosis-inhibitor, rabbit bcl-2, which is useful for enhancing cell survival.

In one aspect of this invention, the non-human transgenic animal which expresses the rabbit bcl-2 apoptosis inhibitor is preferably an animal undergoing short-term lymphopoietic B-cell development discussed above, which includes, but is not limited to, animals like rabbits, chickens, sheep and cows, etc. Since these animals are larger, their antibody production and yields, using the methods described above, are also greater. In another aspect of the invention, the non-human transgenic animal which expresses the Ig locus-self-cleaving peptide-apoptosis inhibitor, is any animal including rodents (e.g. mice, rats), rabbits, birds (e.g. chickens, turkeys, ducks, geese, etc.), cows, pigs, sheep, goats, horses, donkeys and other farm animals. In a further aspect, the transgenic animals used in the methods of the invention can either be gene converting animals or animals that can undergo antibody diversification by gene rearrangement that stops early in life. In a preferred embodiment, the non-human transgenic animal is the rabbit.

Thus, the transgenic constructs, the vectors comprising the transgene constructs and the transgenic animals generated using the methods described above are all embodiments of the invention.

The invention is further illustrated, but by no means limited, by the following examples.

EXAMPLE 1

Construction of a Apoptosis-Inhibitor Expression Vector with Human bcl-2

Screening of rabbit genomic BAC libraries resulted in the identification of two BACs (179L1 and 19602; Gene Bank Accession Nos: AY495827, and AY495828, respectively) containing rabbit light chain K1 gene segments.

For the construction of a B-cell specific apoptosis-inhibitor expression vector, BAC AY495827 was modified by homologous recombination in *E. coli* (ET cloning: E. Chiang Lee et al., *Genomics* 73, 56-65 (2001); Daiguan Yu et al., *PNAS* 97, 5978-5983 (2000); Muyrers et al., *Nucleic Acids Research* 27, 1555-1557 (1999); Zhang et al., *Nature Biotechnology* 18, 1314-1317(2000)) and nucleotides 1-107795 and 142832-205141 were deleted. A synthetic human bcl-2 gene, under control of the kappa 1 promoter from AY495828 (pos. 114284-114570) further connected to the rabbit beta globin polyA sequence, was synthesized. Downstream, a gentamycin selection cassette flanked by FRT-sites was introduced by overlap extension PCR. The bcl-2-gentamycin cassette was amplified with primers having 50 bp homologies to the modified AY495827 BAC (SEQ ID NO: 1). The sequence from nucleotide 134571-136019 on BAC AY495827 was exchanged against the bcl-2-gentamycin cassette (SEQ ID NO: 1) by ET cloning. Positive clones were selected with gentamycin, analyzed by restriction enzyme digests and confirmed by sequencing. Subsequently, the gentamycin selection cassette was removed by FLP-recombination. The resulting construct was used to generate transgenic animals.

EXAMPLE 2

Construction of a Apoptosis-Inhibitor Expression Vector with Mouse bcl-2

Screening of a rabbit genomic BAC libraries resulted in the identification of two BACs (179L1 and 196O2; Gene Bank Accession Nos: AY495827, and AY495828, respectively) containing rabbit light chain K1 gene segments.

For the construction of a B-cell specific apoptosis-inhibitor expression vector, BAC AY495827 was modified by homologous recombination in *E. coli* (ET cloning: (E. Chiang Lee et al., *Genomics* 73, 56-65 (2001); Daiguan Yu et al., *PNAS* 97, 5978-5983 (2000); Muyrers et al., *Nucleic Acids Research* 27, 1555-1557 (1999); Zhang et al., *Nature Biotechnology* 18, 1314-1317(2000) and nucleotides 1-107795 and 142832-205141 were deleted. A synthetic mouse bcl-2 gene under the control of the kappa 1 promoter from AY495828 (pos. 114284-114570), further connected to the rabbit beta globin polyA sequence, was synthesized. Downstream, a gentamycin selection cassette flanked by FRT-sites was introduced by overlap extension PCR. The bcl-2-gentamycin cassette was amplified with primers having 50 bp homologies to the modified AY495827 BAC (SEQ ID NO:1). The sequence from nucleotide 134571-136019 on BAC AY495827 was exchanged against the bcl-2-gentamycin cassette by ET cloning. Positive clones were selected with gentamycin and analyzed by restriction enzyme digests and confirmed by sequencing. Subsequently, the gentamycin selection cassette was removed by FLP-recombination. The resulting construct was used to generate transgenic animals.

EXAMPLE 3

Construction of a Human(ized) Heavy Chain Locus Encoding a Fusion Protein Consisting of the Membrane Forms of IgM and IgG, a 2A Self-Cleaving Peptide, and Apoptosis-Inhibitor BAC and fosmid clones containing rabbit immunoglobulin heavy chain locus sequences were isolated from genomic DNA libraries using probes specific for the constant, variable, and joining gene segments or the 3' enhancer region. Isolated BACs and fosmid Fos15B were sequenced (Genebank acc. No. AY386695, AY386696, AY386697, AY386698). The J and Cμ regions of AY386695 and the C☐ region of AY386696 were exchanged with corresponding human counterparts by homologous recombination in *E. coli* by ET cloning (E. Chiang Lee et al., *Genomics* 73, 56-65 (2001); Daiguan Yu et al., *PNAS* 97, 5978-5983 (2000); Muyrers et al., *Nucleic Acids Research* 27, 1555-1557 (1999); Zhang et al., *Nature Biotechnology* 18, 1314-1317(2000)).

The four BACs were recombined by in vitro ligation and Cre-mediated recombination to reconstitute a rabbit Ig locus with human J, Cμ and C☐ coding sequences.

To link the expression of bcl-2 to the expression of IgM and IgG, the coding sequence of bcl-2 was fused with the coding sequence of M2 membrane exons of IgM and IgG with a sequence coding for a F2A self-cleaving peptide.

For the insertion of a sequence encoding an IgG-M2-F2A-bcl-2 fusion protein the following construct was generated. Sequences for homologous recombination were based on the sequence of BAC AY 386696. A DNA fragment (from 5' to 3') containing a KpnI site, a sequence identical to 50 nucleotides of Cγ M2, a sequence encoding F2A, a sequence encoding a human bcl-2, an FRT5 site, and an EcoRI site was synthesized. The rpsL.Neo counter selection cassette was amplified using plasmid pSC101 rpsL-neo (Genebridges) as template. The upstream primer contained a EcoRI and an FRT5 site, the downstream primer contained a sequence identical to 50 nucleotides downstream of Cγ M2 and a XhoI site. The synthetic fragment and the PCR amplification product were ligated into the pcDNA3.1(+) vector, opened with KpnI and XhoI. The ligated cassette (SEQ ID NO: 2) was released with XhoI and KpnI and used for homologous recombination in *E coli*. Following transformation of the cassette into the *E. coli* strain DH10B containing BAC AY 386696 and the plasmid pSC101-BAD-gba-tetra, expression of recombinases Redα/β was induced. Subsequently, kanamycin resistant clones were selected and were analysed by restriction enzyme digestion and partial sequence analysis. Lastly, the RpsLNeo-resistance gene was deleted from the BAC by Flp-mediated recombination.

The resulting BAC clone was further modified through insertion of a sequence encoding an IgM-M2-F2A-bcl-2 fusion protein. Sequences for homologous recombination are based on the sequence of BAC AY 386696. The rpsL.Neo gene was amplified using plasmid pSC101 rpsL-neo (Genebridges) as the template. Primers contain sequences identical to IgG-M2 and flanking sequences, FRT- and FRT2-sites (SEQ ID NO: 3). The amplification product was inserted into BAC AY 386696 by ET cloning. Subsequently, the selection cassette was replaced with a DNA fragment encoding an IgM-M2-F2A-bcl-2 fusing protein (SEQ ID NO: 4). This DNA fragment was synthesized containing from 5' to 3'—an EcoRI site, an FRT site, a sequence encoding IgM-M2, a sequence encoding F2A and bcl-2, a FRT2 and an EcoRI site (SEQ ID NO: 4). The synthesized fragment was released with EcoRI and was used for the exchange of the rpsL.Neo gene with IgM-M2-F2A-bcl-2 by Flp-mediated recombination between FRT/FRT and FRT2/FRT2 sites. Positive clones are identified by restriction analysis and further analysed by partial sequencing.

The resulting BAC was combined with BACs containing different V-regions. BACs can be combined by ligation or recombination. The resulting constructs were used for the generation of transgenic animals.

EXAMPLE 4

Generation of Transgenic Mice and Rabbits Expressing Humanized Heavy Chain Immunoglobulins Transgenic rabbits and mice containing humanized heavy and light chain immunoglobulin loci and a apoptosis-inhibitor gene are generated by injection of DNA into the pronuclei of fertilized oocytes and subsequent transfer of embryos into foster mothers. Transgenic founder animals are identified by PCR. Expression of human(ized) immunoglobulin M and G is measured by ELISA. Expression of humanized IgG was 10-20 mg/ml.

EXAMPLE 5

Generation of Transgenic Chicken Expressing Humanized Heavy Chain Immunoglobulins Transgenic chicken were generated by testis mediated gene transfer. DNA constructs (50 ug) are mixed with 250 ul lipofection reagent (superfect) in 500 ul 0.9% NaCl and injected in the testis of roosters. Three to four weeks later roosters with transgenic sperm are identified by PCR analysis and mated with hens. Transgenic offspring were identified by PCR. Expression of humanized IgG is 10-20 mg/ml.

All references cited throughout the disclosure along with references cited therein are hereby expressly incorporated by reference.

While the invention is illustrated by reference to certain embodiments, it is not so limited. One skilled in the art will understand that various modifications are readily available and can be performed without substantial change in the way the invention works. All such modifications are specifically intended to be within the scope of the invention claimed herein.

What is claimed is:

1. A transgenic rabbit comprising a polynucleotide comprising an immunoglobulin kappa light chain 3' promoter/enhancer operably linked to a polynucleotide encoding a fusion protein comprising bcl-2 coupled to a membrane form of human IgM by a self-cleaving peptide.

* * * * *

SEQUENCE LISTING

<160> NUMBER OF SEQ ID NOS: 20

<210> SEQ ID NO 1
<211> LENGTH: 2338
<212> TYPE: DNA
<213> ORGANISM: Artificial Sequence
<220> FEATURE:
<223> OTHER INFORMATION: Synthesized sequence

<400> SEQUENCE: 1

```
acataaatat actgtcttcc aggatcttag agctcaccta aggaaacaag agttcatttg      60
aagtttttaa agtgaacctc agtgactttg ggatgtgaac tctccgagta gaagcatgcg     120
cactgcaggt aaacttgtgc agccctggtc tgagctgggg cagctggaga cacagcccct     180
gggctgagtt ctgagctgcc ctgggccctt cagctgggca cagccctgcc ccgcccctgc     240
tcatttgcat gtccccagag caccacccac ctctctgggc atttaggagc aggctgctcc     300
cgccccatgc aggaggcagt gccaggcagg acccagcatg gcgcacgctg ggagaacagg     360
gtacgataac cgggagatag tgatgaagta catccattat aagctgtcgc agaggggcta     420
cgagtgggat gcgggagatg tgggcgccgc gcccccgggg gccgccccg cgccgggcat      480 cttctcctcg cagcccgggc acacgcccca tacagccgca tcccgggacc cggtcgccag     540
gacctcgccg ctgcagaccc cggctgcccc cggcgccgcc gcggggcctg cgctcagccc     600
ggtgccacct gtggtccacc tgaccctccg ccaggccggc gacgacttct cccgccgcta     660
ccgccgcgac ttcgccgaga tgtccaggca gctgcacctg acgcccttca ccgcgcgggg     720
acgctttgcc acggtggtgg aggagctctt cagggacggg gtgaactggg ggaggattgt     780
ggccttcttt gagttcggtg gggtcatgtg tgtggagagc gtcaaccggg agatgtcgcc     840
cctggtggac aacatcgccc tgtggatgac tgagtacctg aaccggcacc tgcacacctg     900
gatccaggat aacggaggct gggatgcctt tgtggaactg tacggcccca gcatgcgcc      960 tctgtttgat ttctcctggc tgtctctgaa gactctgctc agtttggccc tggtgggagc    1020
ttgcatcacc ctgggtgcct atctgggcca caagtgaatc tttttccctc tgccaaaaat    1080 tatgggggaca tcatgaagcc ccttgagcat ctgacttctg gctaataaag gaaatttatt    1140
ttcattgcaa tagtgtgttg gaattttttg tgtctctcac tcggaaggac atatgggagg    1200
gcaaatcatt taaacatca gaatgagtat ttggtttaga gtttgcaac atatgccgaa      1260 gttcctattc cgaagttcct attctctaga aagtatagga acttctggag ttgtagatcc    1320
tctacgccgg acgcatcgtg gccggcatca ccggctgaag gcacgaaccc agttgacata    1380
agcctgttcg gttcgtaaac tgtaatgcaa gtagcgtatg cgctcacgca actggtccag    1440
aaccttgacc gaacgcagcg gtggtaacgg cgcagtggcg gttttcatgg cttgttatga    1500 ctgtttttttt gtacagtcta tgcctcgggc atccaagcag caagcgcgtt acgccgtggg    1560
tcgatgtttg atgttatgga gcagcaacga tgttacgcag cagcaacgat gttacgcagc    1620
agggcagtcg ccctaaaaca aagttaggtg gctcaagtat gggcatcatt cgcacatgta    1680
```

```
ggctcggccc tgaccaagtc aaatccatgc gggctgctct tgatcttttc ggtcgtgagt    1740
tcggagacgt agccacctac tcccaacatc agccggactc cgattacctc gggaacttgc    1800
tccgtagtaa dacattcatc gcgcttgctg ccttcgacca agaagcggtt gttggcgctc    1860
tcgcggctta cgttctgccc aggtttgagc agccgcgtag tgagatctat atctatgatc    1920
tcgcagtctc cggcgagcac cggaggcagg gcattgccac cgcgctcatc aatctcctca    1980
agcatgaggc caacgcgctt ggtgcttatg tgatctacgt gcaagcagat tacggtgacg    2040
atcccgcagt ggctctctat acaaagttgg gcatacggga agaagtgatg cactttgata    2100
tcgacccaag taccgccacc taacaattcg ttcaagccga ggttgtaaca ctggcagagc    2160
attacgctga cttgacggga cggcggcttt gttgaataaa tcgaactttt gctgagttga    2220
aggatcagat cacgcatctt gaagttccta ttccgaagtt cctattctct agaaagtata    2280
ggaacttcga ttcactttta agtagaaatt ttataaagt gggtaaatga gtaggttt      2338
```

<210> SEQ ID NO 2
<211> LENGTH: 2383
<212> TYPE: DNA
<213> ORGANISM: Artificial Sequence
<220> FEATURE:
<223> OTHER INFORMATION: Synthesized sequence

<400> SEQUENCE: 2

```
ggtacctgaa acacaccatc gctcccgact acaggaacat gatcgggcag ggggccgtga      60
aacagacttt gaattttgac cttctcaagt tggcgggaga cgtggagtcc aacccagggc     120
ccatggccca cgccgggcgc actggctatg ataatcgcga aattgtcatg aagtatattc     180
actacaagct ctctcaaaga ggatacgagt gggatgcggg gacgtcggc gctgccccac      240 ctggagctgc gccggctcca ggcatctta gcagccagcc gggccacaca cctcacaccg     300
ctgcctccag ggatccggtg gcacggacca gccctctgca aactcccgcc gccccctgggg   360 ctgcagcggg tcccgccttg tccccggtgc cccctgtggt gcacctcacg ctgcggcagg     420
cgggcgacga cttcagcagg cgctacagaa gagactttgc cgaaatgtcc cgccagctcc     480
atctgacccc cttcaccgca cgagggaggt tcgccaccgt ggtcgaagaa cttttccgcg     540
acggtgtgaa ctggggccgc atcgttgcct tttttgagtt cggggggtt atgtgcgtgg      600 aatcagtgaa ccgcgaaatg agtcccttgg tcgacaacat agctctttgg atgacagagt     660
acctgaaccg gcatctgcat acttggatac aggacaacgg aggatgggat gcttttgttg     720
agctgtacgg cccatcaatg cgccccttgt tcgacttcag ctggttgtcc ctgaagacgc    780
tcctgagcct cgctcttgtg ggcgcctgta tcactttggg cgcctatctc ggacataaat    840
aagaagttcc tattccgaag ttcctattct tcaaaggta taggaacttc gaattcatta    900
caccagtgtc agtaagcggg caaagtcggt taatgtcagt ttcaaaacgt ccacccatca    960
ggcctggtga tgatggcggg atcgttgtat atttcttgac ccttttcgg catcgcccta    1020 aaattcggcg tcctcatatt gtgtgaggac gttttattac gtgttacga agcaaaagct    1080 aaaaccagga gctatttaat ggcaacagtt aaccagctgg tacgcaaacc acgtgctcgc    1140
aaagttgcga aaagcaacgt gcctgcgctg aagcatgcc cgcaaaaacg tggcgtatgt    1200
actcgtgtat atactaccac tcctaaaaaa ccgaactccg cgctgcgtaa agtatgccgt    1260
gttcgtctga ctaacggttt cgaagtgact tcctacatcg gtggtgaagg tcacaacctg    1320
caggagcact ccgtgatcct gatccgtggc ggtcgtgtta agacctcccc gggtgttcgt    1380
taccacaccg tacgtggtgc gcttgactgc tccggcgtta agaccgtaa gcaggctcgt    1440
```

```
tccaagtatg gcgtgaagcg tcctaaggct taaggaggac aatcatgatt gaacaagatg   1500
gattgcacgc aggttctccg gccgcttggg tggagaggct attcggctat gactgggcac   1560
aacagacaat cggctgctct gatgccgccg tgttccggct gtcagcgcag gggcgcccgg   1620
ttctttttgt caagaccgac ctgtccggtg ccctgaatga actgcaggac gaggcagcgc   1680
ggctatcgtg gctggccacg acgggcgttc cttgcgcagc tgtgctcgac gttgtcactg   1740
aagcgggaag ggactggctg ctattgggcg aagtgccggg gcaggatctc ctgtcatctc   1800
accttgctcc tgccgagaaa gtatccatca tggctgatgc aatgcggcgg ctgcatacgc   1860
ttgatccggc tacctgccca ttcgaccacc aagcgaaaca tcgcatcgag cgagcacgta   1920
ctcggatgga agccggtctt gtcgatcagg atgatctgga cgaagagcat caggggctcg   1980
cgccagccga actgttcgcc aggctcaagg cgcgcatgcc cgacgcgag gatctcgtcg   2040 tgacccatgg cgatgcctgc ttgccgaata tcatggtgga aaatggccgc ttttctggat   2100
tcatcgactg tggccggctg gtgtggcgg accgctatca ggacatagcg ttggctaccc   2160
gtgatattgc tgaagagctt ggcggcgaat gggctgaccg cttcctcgtg ctttacggta   2220
tcgccgctcc cgattcgcag cgcatcgcct tctatcgcct tcttgacgag ttcttctgag   2280
aagttcctat tccgaagttc ctattcttca aaaggtatag gaacttcgcc cttcgttctc   2340
acagcctgcc tccctggcca gcaggagccc ccgcctcctc gag                      2383

<210> SEQ ID NO 3
<211> LENGTH: 1579
<212> TYPE: DNA
<213> ORGANISM: Artificial Sequence
<220> FEATURE:
<223> OTHER INFORMATION: Synthesized sequence

<400> SEQUENCE: 3
cgtccattcc caacacatga acagcatctc acgccacctc tgttgcctgc gaagttccta     60
ttccgaagtt cctattctct acttagtata ggaacttcat tacaccagtg tcagtaagcg    120
ggcaaagtcg gttaatgtca gtttcaaaac gtccacccat caggcctggt gatgatggcg    180
ggatcgttgt atatttcttg acaccttttc ggcatcgccc taaaattcgg cgtcctcata    240
ttgtgtgagg acgttttatt acgtgtttac gaagcaaaag ctaaaaccag gagctattta    300
atggcaacag ttaaccagct ggtacgcaaa ccacgtgctc gcaaagttgc gaaaagcaac    360
gtgcctgcgc tggaagcatg cccgcaaaaa cgtggcgtat gtactcgtgt atatactacc    420
actcctaaaa aaccgaactc cgcgctgcgt aaagtatgcc gtgttcgtct gactaacggt    480
ttcgaagtga cttcctacat cggtggtgaa ggtcacaacc tgcaggagca ctccgtgatc    540
ctgatccgtg gcggtcgtgt taaagacctc ccgggtgttc gttaccacac cgtacgtggt    600
gcgcttgact gctccggcgt taaagaccgt aagcaggctc gttccaagta tggcgtgaag    660
cgtcctaagg cttaaggagg acaatcatga ttgaacaaga tggattgcac gcaggttctc    720
cggccgcttg gtggagagg ctattcggct atgactgggc acaacagaca atcggctgct    780
ctgatgccgc cgtgttccgg ctgtcagcgc aggggcgccc ggttcttttt gtcaagaccg    840
acctgtccgg tgccctgaat gaactgcagg acgaggcagc gcggctatcg tggctggcca    900
cgacgggcgt tccttgcgca gctgtgctcg acgttgtcac tgaagcggga agggactggc    960
tgctattggg cgaagtgccg gggcaggatc tcctgtcatc tcaccttgct cctgccgaga   1020 agtatccat catggctgat gcaatgcggc ggctgcatac gcttgatccg gctacctgcc   1080
cattcgacca ccaagcgaaa catcgcatcg agcgagcacg tactcggatg gaagccggtc   1140
```

```
ttgtcgatca ggatgatctg gacgaagagc atcagggggct cgcgccagcc gaactgttcg    1200
ccaggctcaa ggcgcgcatg cccgacggcg aggatctcgt cgtgacccat ggcgatgcct    1260
gcttgccgaa tatcatggtg aaaatggccc gcttttctgg attcatcgac tgtggccggc    1320
tgggtgtggc ggaccgctat caggacatag cgttggctac ccgtgatatt gctgaagagc    1380
ttggcggcga atgggctgac cgcttcctcg tgctttacgg tatcgccgct cccgattcgc    1440
agcgcatcgc cttctatcgc cttcttgacg agttcttctg agaagttcct attccgaagt    1500
tcctattctc tagaaagtat aggaacttcc ctgagaagga tgtcggaggc caagagacaa    1560
gcccgccgtg gccctgctc                                                  1579

<210> SEQ ID NO 4
<211> LENGTH: 902
<212> TYPE: DNA
<213> ORGANISM: Artificial Sequence
<220> FEATURE:
<223> OTHER INFORMATION: Synthesized sequence

<400> SEQUENCE: 4
gaattcgaag ttcctattcc gaagttccta ttctctactt agtataggaa cttcaggtga     60
agcagacttt gaattttgac cttctcaagt tggcgggaga cgtggagtcc aacccagggc    120
ccatggccca cgccgggcgc actggctatg ataatcgcga aattgtcatg aagtatattc    180
actacaagct ctctcaaaga ggatacgagt gggatgcggg ggacgtcggc gcagctccac    240
ctggagctgc gccggcccct ggcatcttta gcagccagcc gggccacaca cctcacaccg    300
ctgcctccag ggatccggtg gcacggacca gccctctgca aactcccgcc gcccctgggg    360
ctgcagcggg tcccgccttg tccccggtgc cccctgtggt gcacctcacg ctgcggcagg    420
cgggcgacga cttcagcagg cgctacagaa gagactttgc cgaaatgtcc cgccagctcc    480
atctgacccc cttcaccgca cgagggaggt tcgccaccgt ggtcgaagaa cttttccgcg    540
acggtgtgaa ctggggccgc atcgttgcct tttttgagtt cggggggggtt atgtgcgtgg    600 aatcagtgaa ccgcgaaatg agtcccttgg tcgacaacat agctctttgg atgacagagt    660
acctgaaccg gcatctgcat acttggatac aggacaacgg aggatgggat gcttttgttg    720
agctgtacgg cccatcaatg cgccccttgt tcgacttcag ctggttgtcc ctgaagacgc    780
tcctgagcct cgctcttgtg ggcgcctgta tcactttggg cgcctatctc ggacataaat    840
aagaagttcc tattccgaag ttcctattct ctagaaagta taggaacttc ctcgaggaat    900
tc                                                                    902

<210> SEQ ID NO 5
<211> LENGTH: 226
<212> TYPE: PRT
<213> ORGANISM: Oryctolagus

<400> SEQUENCE: 5

Met Ala His Ala Gly Arg Thr Gly Tyr Asp Asn Arg Glu Ile Val Met
 1               5                  10                  15

Lys Tyr Ile His Tyr Lys Leu Ser Gln Arg Gly Tyr Glu Trp Asp Ala
            20                  25                  30

Gly Asp Ala Gly Ala Ala Ser Ala Pro Gly Val Phe Ser Ser Gln Pro
        35                  40                  45

Ala Pro Ala Ala Pro Arg Asp Pro Ala Ala Arg Thr Ser Pro Pro Pro
    50                  55                  60

Pro Pro Ala Ala Ala Gly Pro Ala Leu Ser Pro Val Pro Pro Val Val
```

|  |  |  |  | 65 |  |  |  |  | 70 |  |  |  |  | 75 |  |  |  |  | 80 |
|---|---|---|---|---|---|---|---|---|---|---|---|---|---|---|---|---|---|---|---|

His Leu Thr Leu Arg Gln Ala Gly Asp Asp Phe Ser Arg Arg Tyr Arg
                 85                   90                   95

Arg Asp Phe Ala Glu Met Ser Ser Gln Leu His Leu Thr Pro Phe Thr
                100                  105                  110

Ala Arg Gly Arg Phe Ala Thr Val Val Glu Glu Leu Phe Arg Asp Gly
                115                  120                  125

Val Asn Trp Gly Arg Ile Val Ala Phe Phe Glu Phe Gly Gly Val Met
            130                  135                  140

Cys Val Glu Ser Val Asn Arg Glu Met Ser Pro Leu Val Asp Asn Ile
145                 150                  155                  160

Ala Leu Trp Met Thr Glu Tyr Leu Asn Arg His Leu His Thr Trp Ile
                165                  170                  175

Gln Asp Asn Gly Gly Trp Asp Ala Phe Val Glu Leu Tyr Gly Pro Ser
                180                  185                  190

Val Arg Pro Leu Ser Asp Phe Ser Trp Val Ser Leu Lys Thr Leu Phe
            195                  200                  205

Ser Leu Ala Leu Ile Gly Ala Cys Ile Thr Leu Gly Ala Tyr Leu Gly
        210                  215                  220

His Lys
225

<210> SEQ ID NO 6
<211> LENGTH: 788
<212> TYPE: DNA
<213> ORGANISM: Artificial Sequence
<220> FEATURE:
<223> OTHER INFORMATION: Synthesized sequence

<400> SEQUENCE: 6
aggtgaagca gactttgaat tttgaccttc tcaagttggc gggagacgtg gagtccaacc    60
cagggcccat ggcccacgcc gggcgcactg gctatgataa tcgcgaaatt gtcatgaagt   120
atattcacta caagctctct caaagaggat acgagtggga tgcgggggac gtcggcgcag   180
ctccacctgg agctgcgccg gcccctggca tctttagcag ccagccgggc cacacacctc   240
acaccgctgc ctccagggat ccggtggcac ggaccagccc tctgcaaact cccgccgccc   300
ctggggctgc agcgggtccc gccttgtccc cggtgccccc tgtggtgcac ctcacgctgc   360
ggcaggcggg cgacgacttc agcaggcgct acagaagaga ctttgccgaa atgtcccgcc   420
agctccatct gaccccctcc accgcacgag ggaggttcgc caccgtggtc gaagaacttt   480
tccgcgacgg tgtgaactgg ggccgcatcg ttgcctttt tgagttcggg ggggttatgt   540
gcgtggaatc agtgaaccgc gaaatgagtc ccttggtcga aacatagct ctttggatga   600
cagagtacct gaaccggcat ctgcatactt ggatacagga caacggagga tgggatgctt   660
ttgttgagct gtacgcccca tcaatgcgcc ccttgttcga cttcagctgg ttgtccctga   720
agacgctcct gagcctcgct cttgtgggcg cctgtatcac tttgggcgcc tatctcggac   780
ataaataa                                                              788

<210> SEQ ID NO 7
<211> LENGTH: 788
<212> TYPE: DNA
<213> ORGANISM: Artificial Sequence
<220> FEATURE:
<223> OTHER INFORMATION: Synthesized sequence

<400> SEQUENCE: 7

| | |
|---|---:|
| aggtgaagca gactttgaat tttgaccttc tcaagttggc gggagacgtg gagtccaacc | 60 |
| cagggcccat ggcgcacgct gggagaacag ggtacgataa ccgggagata gtgatgaagt | 120 |
| acatccatta taagctgtcg cagaggggct acgagtggga tgcgggagat gtgggcgccg | 180 |
| cgccccgggg ggccgccccc cgcgcgggca tcttctcctc gcagcccggg cacacgcccc | 240 |
| atacagccgc atcccgggac ccggtcgcca ggacctcgcc gctgcagacc ccggctgccc | 300 |
| ccggcgccgc cgcggggcct cgcgctcagcc cggtgccacc tgtggtccac ctgaccctcc | 360 |
| gccaggccgg cgacgacttc tcccgccgct accgccgcga cttcgccgag atgtccaggc | 420 |
| agctgcacct gacgcccttc accgcgcggg gacgctttgc cacggtggtg gaggagctct | 480 |
| tcagggacgg ggtgaactgg gggaggattg tggccttctt tgagttcggt ggggtcatgt | 540 |
| gtgtggagag cgtcaaccgg gagatgtcgc ccctggtgga caacatcgcc ctgtggatga | 600 |
| ctgagtacct gaaccggcac ctgcacacct ggatccagga taacggaggc tgggatgcct | 660 |
| tgtggaact gtacgccccc agcatgcggc ctctgtttga tttctcctgg ctgtctctga | 720 |
| agactctgct cagtttggcc ctggtgggag cttgcatcac cctgggtgcc tatctgggcc | 780 |
| acaagtga | 788 |

<210> SEQ ID NO 8
<211> LENGTH: 869
<212> TYPE: DNA
<213> ORGANISM: Artificial Sequence
<220> FEATURE:
<223> OTHER INFORMATION: Synthesized sequence
<400> SEQUENCE: 8

| | |
|---|---:|
| aggtgaagtg gatcttctcg tccgtggtgg agctgaaaca caccatcgct cccgactaca | 60 |
| ggaacatgat cgggcagggg gccgtgaaac agactttgaa ttttgacctt ctcaagttgg | 120 |
| cgggagacgt ggagtccaac ccagggccca tggcccacgc cggcgcacgt ggctatgata | 180 |
| atcgcgaaat tgtcatgaag tatattcact acaagctctc tcaaagagga tacgagtggg | 240 |
| atgcggggga cgtcggcgct gccccacctg gagctgcgcc ggctccaggc atctttagca | 300 |
| gccagccggg ccacacacct cacaccgctg cctccaggga tccggtggca cggaccagcc | 360 |
| ctctgcaaac tcccgccgcc cctggggctg cagcgggtcc cgccttgtcc ccggtgcccc | 420 |
| ctgtggtgca cctcacgctg cggcaggcgg gcgacgactt cagcaggcgc tacagaagag | 480 |
| actttgccga aatgtcccgc cagctccatc tgaccccctt caccgcacga gggaggttcg | 540 |
| ccaccgtggt cgaagaactt ttccgcgacg gtgtgaactg gggccgcatc gttgcctttt | 600 |
| ttgagttcgg gggggttatg tgcgtggaat cagtgaaccg cgaaatgagt cccttggtcg | 660 |
| acaacatagc tctttggatg acagagtacc tgaaccggca tctgcatact tggatacagg | 720 |
| acaacggagg atgggatgct tttgttgagc tgtacggccc catcaatgcg cccttgttcg | 780 |
| acttcagctg gttgtccctg aagacgctcc tgagcctcgc tcttgtgggc gcctgtatca | 840 |
| ctttgggcgc ctatctcgga cataaataa | 869 |

<210> SEQ ID NO 9
<211> LENGTH: 809
<212> TYPE: DNA
<213> ORGANISM: Artificial Sequence
<220> FEATURE:
<223> OTHER INFORMATION: Synthesized sequence
<400> SEQUENCE: 9

| | |
|---|---:|
| aggtgaagcg agcaaagcga ccggtgaaac agactttgaa ttttgacctt ctcaagttgg | 60 |

-continued

```
cgggagacgt ggagtccaac ccagggccca tggcgcacgc tgggagaaca gggtacgata      120
accgggagat agtgatgaag tacatccatt ataagctgtc gcagaggggc tacgagtggg      180
atgcgggaga gtgtgggcgcc gcgcccccgg gggccgcccc cgcgccgggc atcttctcct     240
cgcagcccgg gcacacgccc catacagccg catcccggga cccggtcgcc aggacctcgc      300
cgctgcagac cccggctgcc cccggcgccg ccgcggggcc tgcgctcagc ccggtgccac      360
ctgtggtcca cctgaccctc cgccaggccg gcgacgactt ctcccgccgc taccgccgcg      420
acttcgccga gatgtccagg cagctgcacc tgacgccctt caccgcgcgg ggacgctttg      480
ccacggtggt ggaggagctc ttcagggacg gggtgaactg ggggaggatt gtggccttct      540
ttgagttcgg tggggtcatg tgtgtggaga gcgtcaaccg ggagatgtcg cccctggtgg      600
acaacatcgc cctgtggatg actgagtacc tgaaccggca cctgcacacc tggatccagg      660
ataacggagg ctgggatgcc tttgtggaac tgtacggccc cagcatgcgg cctctgtttg      720
atttctcctg gctgtctctg aagactctgc tcagtttggc cctggtggga gcttgcatca      780
ccctgggtgc ctatctgggc acaagtga                                         809

<210> SEQ ID NO 10
<211> LENGTH: 884
<212> TYPE: DNA
<213> ORGANISM: Artificial Sequence
<220> FEATURE:
<223> OTHER INFORMATION: Synthesized sequence

<400> SEQUENCE: 10
aggtgaagtg gatcttctcg tccgtggtgg agctgaaaca caccatcgct cccgactaca      60
ggaacatgat cgggcagggg gcccgagcaa agcgaccggt gaaacagact ttgaatttgg     120
accttctcaa gttggcggga gacgtggagt ccaacccagg gccatggcc cacgccgggc      180 gcactggcta tgataatcgc gaaattgtca tgaagtatat tcactacaag ctctctcaaa     240
gaggatacga gtgggatgcg ggggacgtcg gcgctgcccc acctggagct gcgccggctc     300
caggcatctt tagcagccag ccgggccaca cacctcacac cgctgcctcc agggatccgg     360
tggcacggac cagccctctg caaactcccg ccgcccctgg ggctgcagcg ggtcccgcct     420
tgtccccggt gccccctgtg gtgcacctca cgctgcggca ggcgggcgac gacttcagca     480
ggcgctacag aagagacttt gccgaaatgt cccgccagct ccatctgacc cccttcaccg     540
cacgagggag gttcgccacc gtggtcgaag aactttttccg cgacggtgtg aactggggcc     600
gcatcgttgc ctttttttgag ttcgggggggg ttatgtgcgt ggaatcagtg aaccgcgaaa     660
tgagtccctt ggtcgacaac atagctcttt ggatgacaga gtacctgaac cggcatctgc      720
atacttggat acaggacaac ggaggatggg atgcttttgt tgagctgtac ggcccatcaa      780
tgcgcccctt gttcgacttc agctggttgt ccctgaagac gctcctgagc ctcgctcttg      840
tgggcgcctg tatcactttg ggcgcctatc tcggacataa ataa                       884

<210> SEQ ID NO 11
<211> LENGTH: 239
<212> TYPE: PRT
<213> ORGANISM: Homo

<400> SEQUENCE: 11

Met Ala His Ala Gly Arg Thr Gly Tyr Asp Asn Arg Glu Ile Val Met
 1               5                  10                  15
Lys Tyr Ile His Tyr Lys Leu Ser Gln Arg Gly Tyr Glu Trp Asp Ala
             20                  25                  30
```

```
Gly Asp Val Gly Ala Ala Pro Pro Gly Ala Ala Pro Ala Pro Gly Ile
             35                  40                  45

Phe Ser Ser Gln Pro Gly His Thr Pro His Pro Ala Ala Ser Arg Asp
 50                  55                  60

Pro Val Ala Arg Thr Ser Pro Leu Gln Thr Pro Ala Ala Pro Gly Ala
 65                  70                  75                  80

Ala Ala Gly Pro Ala Leu Ser Pro Val Pro Val Val His Leu Ala
                 85                  90                  95

Leu Arg Gln Ala Gly Asp Asp Phe Ser Arg Arg Tyr Arg Gly Asp Phe
                100                 105                 110

Ala Glu Met Ser Ser Gln Leu His Leu Thr Pro Phe Thr Ala Arg Gly
            115                 120                 125

Arg Phe Ala Thr Val Val Glu Glu Leu Phe Arg Asp Gly Val Asn Trp
130                 135                 140

Gly Arg Ile Val Ala Phe Phe Glu Phe Gly Gly Val Met Cys Val Glu
145                 150                 155                 160

Ser Val Asn Arg Glu Met Ser Pro Leu Val Asp Asn Ile Ala Leu Trp
                165                 170                 175

Met Thr Glu Tyr Leu Asn Arg His Leu His Thr Trp Ile Gln Asp Asn
            180                 185                 190

Gly Gly Trp Asp Ala Phe Val Glu Leu Tyr Gly Pro Ser Met Arg Pro
        195                 200                 205

Leu Phe Asp Phe Ser Trp Leu Ser Leu Lys Thr Leu Leu Ser Leu Ala
210                 215                 220

Leu Val Gly Ala Cys Ile Thr Leu Gly Ala Tyr Leu Ser His Lys
225                 230                 235

<210> SEQ ID NO 12
<211> LENGTH: 199
<212> TYPE: PRT
<213> ORGANISM: Mus

<400> SEQUENCE: 12

Met Ala Gln Ala Gly Arg Thr Gly Tyr Asp Asn Arg Glu Ile Val Met
 1               5                  10                  15

Lys Tyr Ile His Tyr Lys Leu Ser Gln Arg Gly Tyr Glu Trp Asp Ala
             20                  25                  30

Gly Asp Ala Asp Ala Ala Pro Leu Gly Ala Ala Pro Thr Pro Gly Ile
             35                  40                  45

Phe Ser Phe Gln Pro Glu Ser Asn Pro Met Pro Ala Val His Arg Asp
 50                  55                  60

Met Ala Ala Arg Thr Ser Pro Leu Arg Pro Leu Val Ala Thr Ala Gly
 65                  70                  75                  80

Pro Ala Leu Ser Pro Val Pro Val Val His Leu Thr Leu Arg Arg
                 85                  90                  95

Ala Gly Asp Asp Phe Ser Arg Arg Tyr Arg Arg Asp Phe Ala Glu Met
                100                 105                 110

Ser Ser Gln Leu His Leu Thr Pro Phe Thr Ala Arg Gly Arg Phe Ala
            115                 120                 125

Thr Val Val Glu Glu Leu Phe Arg Asp Gly Val Asn Trp Gly Arg Ile
130                 135                 140

Val Ala Phe Phe Glu Phe Gly Gly Val Met Cys Val Glu Ser Val Asn
145                 150                 155                 160

Arg Glu Met Ser Pro Leu Val Asp Asn Ile Ala Leu Trp Met Thr Glu
                165                 170                 175
```

```
Tyr Leu Asn Arg His Leu His Thr Trp Ile Gln Asp Asn Gly Gly Trp
            180                 185                 190

Val Gly Ala Cys Leu Val Glu
        195
```

<210> SEQ ID NO 13
<211> LENGTH: 236
<212> TYPE: PRT
<213> ORGANISM: Mus

<400> SEQUENCE: 13

```
Met Ala Gln Ala Gly Arg Thr Gly Tyr Asp Asn Arg Glu Ile Val Met
 1               5                  10                  15

Lys Tyr Ile His Tyr Lys Leu Ser Gln Arg Gly Tyr Glu Trp Asp Ala
            20                  25                  30

Gly Asp Ala Asp Ala Ala Pro Leu Gly Ala Ala Pro Thr Pro Gly Ile
        35                  40                  45

Phe Ser Phe Gln Pro Glu Ser Asn Pro Met Pro Ala Val His Arg Asp
    50                  55                  60

Met Ala Ala Arg Thr Ser Pro Leu Arg Pro Leu Val Ala Thr Thr Gly
65                  70                  75                  80

Pro Ala Leu Ser Pro Val Pro Pro Val Val His Leu Thr Leu Arg Arg
                85                  90                  95

Ala Gly Asp Asp Phe Ser Arg Arg Tyr Arg Arg Asp Phe Ala Glu Met
            100                 105                 110

Ser Ser Gln Leu His Leu Thr Pro Phe Thr Ala Arg Gly Arg Phe Ala
        115                 120                 125

Thr Val Val Glu Glu Leu Phe Arg Asp Gly Val Asn Trp Gly Arg Ile
    130                 135                 140

Val Ala Phe Phe Glu Phe Gly Gly Val Met Cys Val Glu Ser Val Asn
145                 150                 155                 160

Arg Glu Met Ser Pro Leu Val Asp Asn Ile Ala Leu Trp Met Thr Glu
                165                 170                 175

Tyr Leu Asn Arg His Leu His Thr Trp Ile Gln Asp Asn Gly Gly Trp
            180                 185                 190

Asp Ala Phe Val Glu Leu Tyr Gly Pro Ser Met Arg Pro Leu Phe Asp
        195                 200                 205

Phe Ser Trp Leu Ser Leu Lys Thr Leu Leu Ser Leu Ala Leu Val Gly
    210                 215                 220

Ala Cys Ile Thr Leu Gly Ala Tyr Leu Gly His Lys
225                 230                 235
```

<210> SEQ ID NO 14
<211> LENGTH: 154
<212> TYPE: PRT
<213> ORGANISM: Rattus

<400> SEQUENCE: 14

```
Ile His Tyr Lys Leu Ser Gln Arg Gly Tyr Glu Trp Asp Thr Gly Asp
 1               5                  10                  15

Glu Asp Ser Ala Pro Leu Arg Ala Ala Pro Thr Pro Gly Ile Phe Ser
            20                  25                  30

Phe Gln Pro Glu Ser Asn Arg Thr Pro Ala Val His Arg Asp Thr Ala
        35                  40                  45

Ala Arg Thr Ser Pro Leu Arg Pro Leu Val Ala Asn Ala Gly Pro Ala
    50                  55                  60

Leu Ser Pro Val Pro Pro Val Val His Leu Thr Leu Arg Arg Ala Gly
```

```
                 65                  70                  75                  80
Asp Asp Phe Ser Arg Arg Tyr Arg Arg Asp Phe Ala Glu Met Ser Ser
                 85                  90                  95

Gln Leu His Leu Thr Pro Phe Thr Ala Arg Gly Arg Phe Ala Thr Val
                100                 105                 110

Val Glu Glu Leu Phe Arg Asp Gly Val Asn Trp Gly Arg Ile Val Ala
                115                 120                 125

Phe Phe Glu Phe Gly Gly Val Met Cys Val Ser Val Asn Arg Glu
                130                 135                 140

Met Ser Pro Leu Val Asp Asn Ile Ala Leu
145                 150

<210> SEQ ID NO 15
<211> LENGTH: 235
<212> TYPE: PRT
<213> ORGANISM: Felis

<400> SEQUENCE: 15

Met Ala His Ala Gly Arg Thr Gly Tyr Asp Asn Arg Glu Ile Val Met
1               5                   10                  15

Lys Tyr Ile His Tyr Glu Leu Pro Gln Arg Gly Tyr Glu Trp Asp Ala
                20                  25                  30

Gly Asp Ala Gly Ala Ala Pro Pro Gly Ala Ala Pro Ala Pro Gly Ile
                35                  40                  45

Phe Ser Ser Gln Pro Gly Arg Thr Pro Ala Pro Ala Arg Thr Ser Pro
            50                  55                  60

Pro Pro Pro Pro Val Ala Pro Ala Ala Ala Ala Ala Ala Ala Gly Pro
65                  70                  75                  80

Ala Leu Ser Pro Val Pro Pro Val Val His Leu Thr Leu Arg Gln Ala
                85                  90                  95

Gly Asp Asp Phe Ser Arg Arg Tyr Arg Arg Asp Phe Ala Glu Met Ser
                100                 105                 110

Ser Gln Leu His Leu Thr Pro Phe Thr Ala Arg Gly Arg Phe Ala Thr
                115                 120                 125

Val Val Glu Glu Leu Phe Arg Asp Gly Val Asn Trp Gly Arg Ile Val
                130                 135                 140

Ala Phe Phe Glu Phe Gly Gly Val Met Cys Val Glu Gly Val Asn Arg
145                 150                 155                 160

Glu Met Ser Pro Leu Val Asp Asn Ile Ala Leu Trp Met Thr Glu Tyr
                165                 170                 175

Leu Asn Arg His Leu His Thr Trp Ile Gln Asp Asn Gly Gly Trp Asp
                180                 185                 190

Ala Phe Val Glu Leu Tyr Gly Pro Ser Met Gln Pro Leu Phe Asp Phe
                195                 200                 205

Ser Trp Leu Ser Leu Lys Ala Leu Leu Ser Leu Ala Leu Val Gly Ala
            210                 215                 220

Cys Ile Thr Leu Gly Ala Tyr Leu Gly His Lys
225                 230                 235

<210> SEQ ID NO 16
<211> LENGTH: 236
<212> TYPE: PRT
<213> ORGANISM: Canis

<400> SEQUENCE: 16

Met Ala Gln Ala Gly Arg Thr Gly Tyr Asp Asn Arg Glu Ile Val Met
1               5                   10                  15
```

```
Lys Tyr Ile His Tyr Lys Leu Ser Gln Arg Gly Tyr Glu Trp Asp Val
         20                  25                  30

Gly Asp Val Asp Ala Ala Pro Leu Gly Ala Ala Pro Thr Pro Gly Ile
         35                  40                  45

Phe Ser Phe Gln Pro Glu Ser Asn Pro Thr Pro Ala Val His Arg Asp
 50                      55                  60

Met Ala Ala Arg Thr Ser Pro Leu Arg Pro Ile Val Ala Thr Thr Gly
 65                  70                  75                  80

Pro Thr Leu Ser Pro Val Pro Pro Val Val His Leu Thr Leu Arg Arg
                 85                  90                  95

Ala Gly Asp Asp Phe Ser Arg Arg Tyr Arg Arg Asp Phe Ala Glu Met
                100                 105                 110

Ser Ser Gln Leu His Leu Thr Pro Phe Thr Ala Arg Gly Arg Phe Ala
                115                 120                 125

Thr Val Val Glu Glu Leu Phe Arg Asp Gly Val Asn Trp Gly Arg Ile
130                 135                 140

Val Ala Phe Phe Glu Phe Gly Gly Val Met Cys Val Glu Ser Val Asn
145                 150                 155                 160

Arg Glu Met Ser Pro Leu Val Asp Asn Ile Ala Leu Trp Met Thr Glu
                165                 170                 175

Tyr Leu Asn Arg His Leu His Thr Trp Ile Gln Asp Asn Gly Gly Trp
                180                 185                 190

Asp Ala Phe Val Glu Leu Tyr Gly Pro Thr Met Gln Pro Leu Phe Asp
                195                 200                 205

Phe Ser Trp Leu Ser Leu Lys Ala Leu Leu Ser Leu Ala Leu Val Gly
210                 215                 220

Ala Cys Ile Thr Leu Gly Ala Tyr Leu Gly His Lys
225                 230                 235

<210> SEQ ID NO 17
<211> LENGTH: 229
<212> TYPE: PRT
<213> ORGANISM: Bos

<400> SEQUENCE: 17

Met Ala His Ala Gly Gly Thr Gly Tyr Asp Asn Arg Glu Ile Val Met
 1               5                  10                  15

Lys Tyr Ile His Tyr Lys Leu Ser Gln Arg Gly Tyr Glu Trp Asp Ala
         20                  25                  30

Gly Asp Ala Gly Ala Ala Pro Pro Gly Ala Ala Pro Ala Pro Gly Ile
         35                  40                  45

Leu Ser Ser Gln Pro Gly Arg Thr Pro Ala Pro Ser Arg Thr Ser Pro
 50                      55                  60

Pro Pro Pro Ala Ala Ala Gly Pro Ala Pro Ser Pro Val Pro
 65                  70                  75                  80

Pro Val Val His Leu Thr Leu Arg Gln Ala Gly Asp Asp Phe Ser Arg
                 85                  90                  95

Arg Tyr Arg Arg Asp Phe Ala Glu Met Ser Ser Gln Leu His Leu Thr
                100                 105                 110

Pro Phe Thr Ala Arg Glu Arg Phe Ala Thr Val Val Glu Glu Leu Phe
                115                 120                 125

Arg Asp Gly Val Asn Trp Gly Arg Ile Val Ala Phe Phe Glu Phe Gly
                130                 135                 140

Gly Val Met Cys Val Glu Ser Val Asn Arg Glu Met Ser Pro Leu Val
145                 150                 155                 160
```

```
Asp Ser Ile Ala Leu Trp Met Thr Glu Tyr Leu Asn Arg His Leu His
                165                 170                 175

Thr Trp Ile Gln Asp Asn Gly Gly Trp Asp Ala Phe Val Glu Leu Tyr
            180                 185                 190

Gly Pro Ser Met Arg Pro Leu Phe Asp Phe Ser Trp Leu Ser Leu Lys
        195                 200                 205

Ala Leu Leu Ser Leu Ala Leu Val Gly Ala Cys Ile Thr Leu Gly Ala
    210                 215                 220

Tyr Leu Gly His Lys
225
```

<210> SEQ ID NO 18
<211> LENGTH: 236
<212> TYPE: PRT
<213> ORGANISM: Cricetulus
<220> FEATURE:
<221> NAME/KEY: VARIANT
<222> LOCATION: 215
<223> OTHER INFORMATION: Xaa = Any Amino Acid

<400> SEQUENCE: 18

```
Met Ala Gln Ala Gly Arg Thr Gly Tyr Asp Asn Arg Glu Ile Val Met
 1               5                  10                  15

Lys Tyr Ile His Tyr Lys Leu Ser Gln Arg Gly Tyr Glu Trp Asp Val
            20                  25                  30

Gly Asp Val Asp Ala Ala Pro Leu Gly Ala Ala Pro Thr Pro Gly Ile
        35                  40                  45

Phe Ser Phe Gln Pro Glu Ser Asn Pro Thr Pro Ala Val His Arg Asp
    50                  55                  60

Met Ala Ala Arg Thr Ser Pro Leu Arg Pro Ile Val Ala Thr Thr Gly
65                  70                  75                  80

Pro Thr Leu Ser Pro Val Pro Val Val His Leu Thr Leu Arg Arg
                85                  90                  95

Ala Gly Asp Asp Phe Ser Arg Arg Tyr Arg Arg Asp Phe Ala Glu Met
                100                 105                 110

Ser Ser Gln Leu His Leu Thr Pro Phe Thr Ala Arg Gly Arg Phe Ala
            115                 120                 125

Thr Val Val Glu Glu Leu Phe Arg Asp Gly Val Asn Trp Gly Arg Ile
        130                 135                 140

Val Ala Phe Phe Glu Phe Gly Gly Val Met Cys Val Glu Ser Val Asn
145                 150                 155                 160

Arg Glu Met Ser Pro Leu Val Asp Asn Ile Ala Leu Trp Met Thr Glu
                165                 170                 175

Tyr Leu Asn Arg His Leu His Thr Trp Ile Gln Asp Asn Gly Gly Trp
            180                 185                 190

Asp Ala Phe Val Glu Leu Tyr Gly Pro Ser Val Arg Pro Leu Phe Asp
        195                 200                 205

Phe Ser Trp Leu Ser Leu Xaa Thr Leu Leu Asn Leu Ala Leu Val Gly
    210                 215                 220

Ala Cys Ile Thr Leu Gly Thr Tyr Leu Gly His Lys
225                 230                 235
```

<210> SEQ ID NO 19
<211> LENGTH: 233
<212> TYPE: PRT
<213> ORGANISM: Gallus

<400> SEQUENCE: 19

```
Met Ala His Pro Gly Arg Arg Gly Tyr Asp Asn Arg Glu Ile Val Leu
1               5                   10                  15

Lys Tyr Ile His Tyr Lys Leu Ser Gln Arg Gly Tyr Asp Trp Ala Ala
            20                  25                  30

Gly Glu Asp Arg Pro Pro Val Pro Pro Ala Pro Ala Pro Ala Ala Ala
        35                  40                  45

Pro Ala Ala Val Ala Ala Ala Gly Ala Ser Ser His His Arg Pro Glu
    50                  55                  60

Pro Pro Gly Ser Ala Ala Ala Ser Glu Val Pro Pro Ala Glu Gly Leu
65                  70                  75                  80

Arg Pro Ala Pro Pro Gly Val His Leu Ala Leu Arg Gln Ala Gly Asp
                85                  90                  95

Glu Phe Ser Arg Arg Tyr Gln Arg Asp Phe Ala Gln Met Ser Gly Gln
            100                 105                 110

Leu His Leu Thr Pro Phe Thr Ala His Gly Arg Phe Val Ala Val Val
        115                 120                 125

Glu Glu Leu Phe Arg Asp Gly Val Asn Trp Gly Arg Ile Val Ala Phe
130                 135                 140

Phe Glu Phe Gly Gly Val Met Cys Val Glu Ser Val Asn Arg Glu Met
145                 150                 155                 160

Ser Pro Leu Val Asp Asn Ile Ala Thr Trp Met Thr Glu Tyr Leu Asn
            165                 170                 175

Arg His Leu His Asn Trp Ile Gln Asp Asn Gly Gly Trp Asp Ala Phe
        180                 185                 190

Val Glu Leu Tyr Gly Asn Ser Met Arg Pro Leu Phe Asp Phe Ser Trp
    195                 200                 205

Ile Ser Leu Lys Thr Ile Leu Ser Leu Val Leu Val Gly Ala Cys Ile
    210                 215                 220

Thr Leu Gly Ala Tyr Leu Gly His Lys
225                 230

<210> SEQ ID NO 20
<211> LENGTH: 44
<212> TYPE: PRT
<213> ORGANISM: Artificial Sequence
<220> FEATURE:
<223> OTHER INFORMATION: Synthesized sequence

<400> SEQUENCE: 20

Asp Ala Phe Val Glu Leu Tyr Gly Pro Ser Val Arg Pro Leu Ser Asp
1               5                   10                  15

Phe Ser Trp Val Ser Leu Lys Thr Leu Phe Ser Leu Ala Leu Ile Gly
            20                  25                  30

Ala Cys Ile Thr Leu Gly Ala Tyr Leu Gly His Lys
        35                  40
```